US008600135B2

(12) United States Patent
Patriarche et al.

(10) Patent No.: US 8,600,135 B2
(45) Date of Patent: Dec. 3, 2013

(54) SYSTEM AND METHOD FOR AUTOMATICALLY GENERATING SAMPLE POINTS FROM A SERIES OF MEDICAL IMAGES AND IDENTIFYING A SIGNIFICANT REGION

(75) Inventors: Julia W. Patriarche, Waipahu, HI (US); Bradley J. Erickson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 781 days.

(21) Appl. No.: 12/648,132

(22) Filed: Dec. 28, 2009

(65) Prior Publication Data

US 2010/0195883 A1 Aug. 5, 2010

Related U.S. Application Data

(63) Continuation-in-part of application No. PCT/US2008/068826, filed on Jun. 30, 2008.

(60) Provisional application No. 60/946,814, filed on Jun. 28, 2007, provisional application No. 61/141,195, filed on Dec. 29, 2008.

(51) Int. Cl.
  *G06K 9/00* (2006.01)
  *A61B 5/05* (2006.01)
(52) U.S. Cl.
  USPC .................... 382/131; 382/128; 600/414
(58) Field of Classification Search
  USPC ................... 382/128–132; 600/410
  See application file for complete search history.

(56) References Cited

U.S. PATENT DOCUMENTS

| 6,272,370 | B1 | 8/2001 | Gillies et al. |
| 7,048,716 | B1 | 5/2006 | Kucharczyk et al. |
| 2005/0197560 | A1* | 9/2005 | Rao et al. ............ 600/410 |
| 2006/0088836 | A1 | 4/2006 | Wohlgemuth et al. |
| 2006/0127880 | A1 | 6/2006 | Harris et al. |
| 2007/0165921 | A1* | 7/2007 | Agam et al. .......... 382/128 |
| 2008/0212864 | A1* | 9/2008 | Bornefalk .......... 382/132 |
| 2009/0080734 | A1* | 3/2009 | Moriya et al. ........ 382/128 |

OTHER PUBLICATIONS

Jinyoung et al ("Segmentation of Brain Parenchyma using Bilateral Filtering and Region Growing", IEEE Aug. 23-26, 2007, pp. 6263-6266).*

(Continued)

*Primary Examiner* — Amara Abdi
(74) *Attorney, Agent, or Firm* — Quarles & Brady LLP

(57) ABSTRACT

A system and method for automatically generating sample points from a series of medical images and identifying a significant region are presented. An image acquisition system acquires the medical images of a region of interest (ROI) and an automated mask generator reviews the images to generate a parenchyma mask. Using the parenchyma mask, an automated sample point generator then detects portions of the medical images indicative of a material expected to be in a ROI and designates sample points therefrom. A target-tissue identification system uses the sample points to create a mathematical description of a target tissue and an enhanced target-tissue. A target-tissue change detection system then detects changes in the mathematical descriptions from those created using prior images. Finally, a significant region detector, which includes a training process to generate a quantitative definition of significance, automatically identifies a significant object in the series of medical images.

15 Claims, 19 Drawing Sheets

(56) References Cited

OTHER PUBLICATIONS

Patriarche, Julia et al. "A Review of the Automated Detecting of Change in Serial Imaging Studies of the Brain." Journal of Digital Imaging, vol. 17, No. 3 Sep. 2004: pp. 158-174.

Erickson, Bradley J. "New Opportunities in Computer-Aided Diagnosis: Change Detection and Characterization." American College of Radiology, 2006: pp. 468-469.
PCT/US2008/068826. International Search Report and the Written Opinion of the International Searching Authority. Dated Oct. 20, 2008. pp. 1-8.

* cited by examiner

SYSTEM AND METHOD FOR AUTOMATICALLY GENERATING SAMPLE POINTS FROM A SERIES OF MEDICAL IMAGES AND IDENTIFYING A SIGNIFICANT REGION

CROSS-REFERENCE TO RELATED APPLICATIONS

This application is a continuation-in-part of co-pending Patent Cooperation Treaty Application Serial No. PCT/US2008/068826, filed Jun. 30, 2008, and entitled "SYSTEM AND METHOD FOR AUTOMATICALLY DETECTING CHANGE IN A SERIES OF MEDICAL IMAGES OF A SUBJECT OVER TIME," which claims the benefit of U.S. Provisional Patent Application Ser. No. 60/946,814, filed on Jun. 28, 2007, and entitled "AUTOMATED DETECTION OF CHANGE IN SERIAL IMAGING STUDIES OF THE BRAIN," both of which are incorporated herein by reference.

This application also claims the benefit of U.S. Provisional Patent Application Ser. No. 61/141,195, filed on Dec. 29, 2008, and entitled "SYSTEM AND METHOD FOR AUTOMATICALLY GENERATING SAMPLE POINTS FROM A SERIES OF MEDICAL IMAGES AND IDENTIFYING A SIGNIFICANT REGION," which is incorporated herein by reference.

STATEMENT REGARDING FEDERALLY SPONSORED RESEARCH

This invention was made with government support under Grant No. NS007494 awarded by the National Institute of Neurological Disorders and Stroke and LM007041 awarded by the National Library of Medicine. The United States Government has certain rights in this invention.

BACKGROUND OF THE INVENTION

The field of the invention is nuclear magnetic resonance imaging methods and systems. More particularly, the invention relates to a system and method for tracking physical changes in a series of medical images of a given patient over time.

When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a magnetic field (excitation field $B_1$) that is in the x-y plane and that is near the Larmor frequency, the net aligned moment, Mz, may be rotated, or "tipped", into the x-y plane to produce a net transverse magnetic moment Mt. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received nuclear magnetic resonance (NMR) signals are digitized and processed to reconstruct the image using one of many well known reconstruction techniques.

A magnetic resonance imaging (MRI) system may be used to acquire many types of images from a particular anatomical structure, for example, the brain. Such images employ contrast mechanisms that enable different brain tissues and lesions to be identified. The usual practice is to acquire a set of MRI images and then manually segment different tissues and lesions and provide sample points of the different tissues for use in subsequent processing. Only limited attempts have been made to implement automated sample point generation algorithms. Some classification algorithms provide very rudimentary automated sample points generation, with little use of domain specific knowledge (e.g., fuzzy k-means), where the user supplies the number of pure tissues and the algorithm attempts to locate the cluster centroids by examining only the image intensities.

Atlas based segmentation methods can be used as one method for the automatic generation of samples, and there have been examples of such implementations in the literature (e.g., Linguraru et al., 2006). However, by definition these atlas based algorithms make assumptions regarding anatomy, which may not be true considering pathology and surgical interventions. One important motivation for the performance of anatomical magnetic resonance imaging and image analysis is the examination of pathology (e.g. tumors, multiple sclerosis, etc.). In such cases, pathology may be quite widespread, and may present in a large variety of ways, causing deviations from "normal" anatomy. Furthermore, resections may be performed in such cases, as well, causing the particular patient's brain to deviate even further from the atlas-based norms.

Classification of lesions, per se, is not new, and many solutions to classify multi-spectral data exist, both within and outside of the domain of medical imaging. Some classification methods are supervised and require that the user supply sample data. Some examples of supervised classification algorithms are thresholding, Euclidean distance, Mahalanobis distance, K nearest neighbor, Bayesian, and neural network. Other classification algorithms are unsupervised and require no sample data. Some examples of unsupervised classification algorithms include chain method, and k-means. It should be noted, however, that unsupervised classification algorithms typically require some rudimentary data be supplied by the user. For example, the chain method requires that a threshold be supplied, and k-means requires that the actual number of clusters be supplied. Some classification algorithms categorize each data point, that is, each voxel in the case of image data, into one of a number of discrete categories. Other classification algorithms allow partial membership in multiple categories. Still, other classification algorithms allow partial membership in multiple classes initially, but then defuzzify the membership data into discrete categories in a later step.

A large fraction of existing classification algorithms are devoted to correctly assigning voxels into discrete categories. In fact, many authors write explicitly that the purpose of classification is to assign multispectral data points into discrete categories and some then add as an after-thought that the assignment may also be made fuzzy. Furthermore, even the algorithms that purport to possess fuzzy classification capability, still have a stated purpose of achieving the highest accuracy with voxels that do in fact belong purely to one category or another, such as Mahalanobis distance based classifiers. These algorithms acknowledge that in their intended domain, the overwhelming majority of voxels will, in fact, belong purely to one category or another and; therefore, in order to achieve the highest average accuracy, these methods use membership functions that achieve the highest accuracy for voxels that are in fact purely one category. However, this is achieved at the expense of accuracy for voxels that do in fact possess mixed membership.

In the case of lesions of the white matter of the brain, the voxels that, in fact, possess partial membership are the voxels that are of greatest interest. There are a variety of reasons for an algorithm to be developed that is focused on accurately quantifying partial membership and partial character, rather than categorizing voxels into discrete categories. For example, in the case of pathology (lesion and enhancing lesion), voxels are rarely fully abnormal. Rather, in such cases, abnormality exists in degree. It is subtly abnormal voxels for which computational assistance might find a high degree of usefulness, because these subtly abnormal voxels are relatively difficult to see with the unaided eye. Furthermore, accurate quantification of these partial volume and partial membership characteristics is important, because it has been shown that, at least in tumors, the rate of growth is suggestive of prognosis. Thus, particularly for small lesions, the ability to accurately quantify these effects places a distinct theoretical lower bound on the size of the lesions from which prognosis may be quantified.

One group of authors created a classification procedure specifically geared for recognizing lesions that acknowledged the importance of preserving partial volume effects via a feature extraction step involving a linear combination of the original images (Hamid Soltanian-Zadeh, 1998). These authors did not, however, design their algorithm with the real behavior of lesion intensities in feature space in mind. Rather, the algorithm, which used an Eigenimage feature extraction step, was more tuned to the behavior of noise and contrast, than the lesions themselves. The algorithm required that the images demonstrate frank lesion and that manual sample points be supplied, which required an investment of time by the user and that introduced variability into the process. Furthermore, the authors used thresholding as their noise reduction scheme.

It has been recognized for a considerable period of time that it is challenging for a human observer to compare images side by side that are nearly the same, in order to identify the differences. This problem exists in a large number of fields of imaging, both within and outside of medicine. Some examples of non-medical change detection topics include remote sensing, astronomy, surveillance, geology, reconnaissance photography, and the like. The development of computer algorithms to compare serial images has been a fruitful field of study in a variety of areas. Probably the most work has been done in the field of remote sensing, where satellite imagery of the earth, using various kinds of sensors, has been used in an attempt to detect various kinds of changes. In this sub-discipline of change detection as in others, imagery is to be compared between image sets acquired at two time-points. The various sub-fields of change detection have important points in common. First, the motivation for change detection is generally the same in all cases. Side-by-side presentation of images for the purposes of identifying small differences is a sub-optimal method of display, because it requires the viewer to sequentially examine each area and each feature to be compared. Second, imaging systems, which include sensors, data storage facilities, and the like, are becoming more and more prevalent and more and more capable of storing vast amounts of data. This phenomena has been called "information overload" and there is little doubt that this trend will continue. With vast amounts of data being collected, it will be unreasonable or impossible for a human to make every imaginable comparison, but it is not at all unreasonable for this task to be performed by computer.

There are a variety of reasons that the comparison of serial images is challenging. One reason that the problem of change detection is difficult is that side-by-side presentation of images is poorly matched to our visual systems. That is, the particular workings of our visual systems means that observers much sequentially examine each feature of interest, and explicitly compare them. This is time consuming, particularly as the data sets and features of interest become large, and it additionally biases us against detecting changes that we do not expect, but which nonetheless may still be relevant and important. Another reason that change detection is challenging is that the disease related changes of interest are likely to be confounded with acquisition related changes, which are not of interest. Still another reason is that comparisons that might be desired are more complicated than simple comparison of the intensities in the images. With greater and greater complexity of the questions to be asked and the comparisons to be made, the task becomes more and more difficult for an unaided observer. Yet another reason the task of comparison of images is difficult is, as mentioned above, information overload. Information overload is a problem that will almost definitely increase as the sophistication of imaging hardware improves.

In its simplest form, change detection may be performed as subtraction of two serial images as shown in FIG. 1. This approach has been used with great effectiveness. More sophisticated approaches may be imagined and have been used, where some processing is performed on the images, to produce derivative data that is then compared as shown in FIG. 2. Spatial registration is a simple example of such processing, which is commonly applied in remote sensing, and medical image analysis. A large variety of image processing steps exist, and can be conceived of. These may require multiple steps in a sequence, for example, inhomogeneity correction followed by registration, followed by some form of image understanding, for example, classification in remote sensing or medical imaging, followed by comparison of the classified images. In the case of surveillance, where it could, for example, be desired to observe when a new person has entered the visual field of the camera, face recognition may be one of the steps. Typically, the more sophisticated processing steps apply domain specific knowledge. The domain specific knowledge, which is used to improve the performance of change detection algorithms and to attune the algorithm to the detection of specific kinds of changes of interest, may be very sophisticated and varies greatly from application to application.

However, the behavior of the sensors, the meaning of intensities, the subject being imaged, and the like vary greatly from domain to domain and, thus, while papers in the field of remote sensing may compare log-ratio images, these may not make any sense at all in the context of comparison of serial MRI brain studies. Likewise, even within brain MRI, the subject of change detection is made broad by the different kinds of domain-specific knowledge that may be applied, and the kind of derivative information that may be generated and compared from one acquisition to another. One set of analyses might be used to detect and characterize changes in white matter lesions, while a completely different set of analyses may be used to detect and characterize changes due to atrophy, for example, identification of discrete boundaries using finite element models with sub-voxel resolution, and the comparison of the position of these boundaries from one acquisition to another. In fact, there exists a large range of possible formulations of these post-acquisition processing steps and inter time-point comparisons.

Within the context of change detection in brain MRI of white matter pathology, there are a variety of causes of inter-observer variability. One is that there is presently no objective definition of stability or progression. Additionally, changes that are relatively subtle, either in extent or degree, may be difficult to see. This is especially true when the images are displayed side-by-side, not registered, with intensity inhomogeneities and the like. Manually identifying changes in such a context requires the observer to mentally deconfound the data, which is challenging for a human observer. It can be imagined that a computer might be very well suited to helping with this task, since, theoretically, computers have unlimited memory, which is in stark contrast with human visual memory and short-term memory, both of which are limited. Thus, computers can apply a theoretically unlimited number of intermediate processing steps. Changes might be spread across multiple pulse sequences, and they might be indefinite in one slice, but more definite in consideration of multiple slices. This, however, requires assimilation and integration of a number of slices, before reaching a decision. Such a process is not natively simple for the human visual system, at least when the images are displayed as slices. However, such a process is much simpler for a computer.

There are other "expectation-oriented" reasons that change detection is challenging. Changes that occur in unexpected locations or that are unexpected in terms of their character, may be missed. There are a variety of other issues that might cause a neuroradiologist to miss changes, such as "satisfaction of search," where a radiologist stops looking when they find imaging features that explain the symptoms motivating the scan in the first place; however, there may still be other important findings in the images. Sometimes, "information overload" makes change detection difficult, due simply to the shear volume of data presented. This problem will almost definitely increase as scanners produce greater and greater quantities of data. In a general sense, computers excel at methodically wading through large amounts of data, looking for needles in hay-stacks, integrating large amounts of data at once, applying serial processing steps, analyzing data mathematically, and bringing noteworthy observations to the attention of the neuroradiologist.

The detection of regions of signal embedded in zero-mean background noise is a recurring problem in various fields of medical imaging, including classification, fMRI, and change detection. The detection of such signals is also an important problem outside of medical imaging in such fields as remote sensing, surveillance, astronomy, and geology, to name a few. A variety of approaches have been taken to identify regions of signal indicating a desired objects embedded in regions of noise in imagery data. By far the most common method that has been used is simple thresholding, where pixels or voxels possessing image intensities lower than some threshold value are set to 0, while image intensities larger than the threshold value are retained. That is, image intensities below the threshold are identified as pixels or voxels are considered to not belong to the object and those above the threshold are considered to belong to the object. Thresholding is limited in that it does not allow simultaneous rejection of noise concurrent with retention of low intensity object voxels. One attempt to approach this limitation is commonly used in fMRI circles. It involves the use of a "smearing" filter on the image data prior to thresholding. Essentially, this approach has two effects. First, it smears the voxel intensities of regions containing actual objects into their neighbors. If the regions of actual objects contain some high intensity voxels, these high intensities can reinforce their low intensity neighbors, which then become included in the region retained by thresholding. The second effect of these smearing filters is for regions not containing actual objects, which presumably contain zero-mean noise, to diminish in intensity. In many cases, this increases the degree to which noisy regions are rejected by the process of thresholding. Although popular in some circles, this approach is in many ways intuitively unsatisfactory. This is primarily because it works most effectively when the actual object possesses high intensity, which is certainly not always the case, rather, it is very frequently desired to detect subtle objects. This is also because the method virtually guarantees the erroneous detection of a penumbra of noise voxels around an intense object. Furthermore, such a method can result in false negatives. That is, if dark voxels around a moderately bright object are smeared into the moderately bright object, the intensities of the voxels making up the moderately bright object to drop below the threshold.

Another filtering approach that has been used involves the application of anisotropic diffusion filters to effect the blurring. Anisotropic diffusion filters are somewhat like low pass filters, except that the blurring is reduced in regions where the gradient of the voxel intensities is high, for example, edges. In cases where objects possess edges, for example, discrete anatomical structures, such an approach might be helpful. However, there are cases where the objects of interest do not possess definite edges at their periphery or where the objects themselves are heterogeneous internally. In the case of objects with very low mean intensities, with mean intensities close to zero and intensity distributions close to or within the level of noise, any gradients surrounding the objects will almost surely exist at a very low level. In each of these cases, an anisotropic diffusion filter would demonstrate limited effectiveness. On the positive side, an anisotropic diffusion filter might be expected to help to reduce the zero mean noise of the background, and in that respect it might aid in the use of simple thresholding to accomplish noise rejection. However, this approach significantly reduces the background noise using an anisotropic diffusion filter that may require the application of multiple iterations of the filter, which causes a significant penumbra of falsely detected voxels around the actual objects. Furthermore, anisotropic diffusion filters are highly parameter dependent, which is inconsistent with applications that desire automation and robustness. Some groups have used edge-finding algorithms themselves with no blurring to identify objects; however, as with anisotropic diffusion filters, these methods do not work when the objects do not possess external edges.

Fuzzy connectedness is a method that has been used to identify objects in images. In practical terms, fuzzy connectedness requires sample points, which is also inconsistent with systems that desire automation. Fuzzy connectedness still hinges on the memberships of single voxels, which is weakest link in the chain, in the terms of the creators of the method. The goal is to identify regions of voxels potentially possessing intensities within the level of the noise floor. By emphasizing the use of chains of connectedness, fuzzy connectedness does not simultaneously emphasize the relative positions of the neighbors with respect to trial voxels and relative to one another. This means that fuzzy connectedness does not make use of the a priori knowledge that one trait of real-world objects is spatial continuity. For example, real world regions or objects in brain MRI images tend to be fat, at least compared to a long, thin, winding chain, and not full of holes. Fuzzy connectedness also does not provide the ability to weigh the size of a region against the memberships of its constituent voxels.

Another prior method in which voxels are accepted as belonging to objects and not belonging to background noise, determines not only whether they exceed a threshold, but some number of their neighbors also exceed the threshold. This method is interesting in as much as it is an initial attempt to balance spatial extent against magnitude of voxel value, in order to establish whether or not a voxel belongs to a real underlying object or whether its intensity is due only to noise. Another method uses fixed dimension kernels, for example, 3×3×3 voxels, and applies a test of significance to help reduce false positives. This method is interesting for the same reasons as the prior method, but this method additionally enforces a higher degree of spatial continuousness. The restricted shape and extent of the regions used by this method, however, make it un-ideal. Another method, demonstrated in the context of surveillance, divides the overall image area into fixed test areas, for example, 4×3 voxels in extent, and applies formal statistical tests to compare the intensity distributions contained by the regions at two time-points, in order to establish whether the contents of each region are the same or different from one time point to the next. This is an interesting approach, for its use of formal statistical tests to decide whether a change had occurred or not. As above, however, the use of fixed position and size test areas is unnecessarily limiting.

Therefore, it would be desirable to have a system and method for accurately and consistently analyzing medical images that does not fall prey to the above-discussed drawbacks.

SUMMARY OF THE INVENTION

The present invention overcomes the aforementioned drawbacks by providing a system for detecting changes in medical images, for example, changes in target tissues as measured by a series of magnetic resonance imaging (MRI) images. More particularly, it includes a mask generator for generating the initial parenchyma and, optionally, cerebrospinal fluid (CSF) and a sample point generator that identifies sample pixels in MRI images that represent different types of tissues. The system also includes a target tissue, for example, lesion, detector that identifies and quantifies tissues, such as abnormal tissues, using the sample pixels. A target-tissue change detector compares target tissues identified currently with previously identified target tissues. In addition, an object boundary identification process may be used with the system to reduce the effects of noise and more definitively identify target tissue boundaries and changes.

In accordance with one aspect of the present invention, a method is disclosed that automatically, repeatably, and reliably generates sample points and initial parenchyma and CSF masks from brain MRI images, which are suitable for use as input to a variety of image processing methods. The method is designed to use simple and reliable knowledge regarding the brain and magnetic resonance images, so that it functions normally regardless of pathology, interventions, or particulars of the acquisition, such as changes in the specific scanner or acquisition parameters. The method is capable of generating samples for the normal tissues, including normal appearing white matter (NAWM), gray matter, and cerebrospinal fluid, as well as the pathological "tissue" enhancing lesion. The "samples" that it generates for the pathological "tissue" referred to as "lesion" are implicit from the above samples. The method is designed to deliver input to lesion finding and change detection methods. The output, however, is equally and fully applicable to a variety of other image processing methods, including registration, inhomogeneity correction, tessellation of surfaces for rendering or other purposes, segmentation for volume computation or other purposes, and the like. The method can be fully automated in that it does not require any user input and it is designed to be flexible enough that it does not require that image volumes supplied to it be acquired using particular hardware or acquisition parameters.

The sample point generation method, in contrast with more sophisticated atlas based segmentation methods, makes only very limited assumptions regarding anatomy, and is thus very flexible with respect to changes due to acquisition, disease, and interventions, such as resections. Use of simple but reliable knowledge makes the method very likely to provide highly accurate results. The present method, if used in a pipeline or spiral step prior to an atlas segmentation method, can also provide a means for an atlas based segmentation algorithm to understand some presented images more clearly, in spite of acquisition related variations. It allows the atlas-based algorithms to understand the images in terms of tissues such as gray matter, white matter, CSF, lesions, and enhancing lesions, instead of in terms of image intensities.

Another aspect of the invention is a method that identifies lesions, both T1-T2 abnormalities, and enhancing lesions, in the white matter of the brain, and to describe these lesions quantitatively. The lesions identified by this method may originate from primary or metastatic tumors, multiple sclerosis, or some other white matter disease process. The method can be fully automated and reproducible, and is highly robust against variations in acquisition parameters, the particulars of the scanner, and the like. From the original input volumes, for example, T1, T1-Post Gadolinium, T2, and the like, the method generates membership images for the classes, such as, lesion and enhancing lesion. On a voxel-by-voxel basis, these memberships vary in value from 0.0 to 1.0. As such, they may be straightforwardly used to compute measures of lesion load.

The lesion identification method is specifically designed to be most accurate in quantifying the memberships of voxels. To the greatest degree possible, the partial membership model is not intended to cater to a priori probabilities, but instead, the algorithm's model of partial-membership effects are derived from a physical model of the behavior of the imaging system. The intended purpose of the method is to quantify these partial memberships and partial characters in only two classes, for example, white matter lesion and enhancing lesion of the brain in magnetic resonance imaging studies. By focusing on this narrow but important topic, the algorithm is able to take advantage of a developed knowledge base.

The lesion identification method has been designed for the specific purpose of producing reproducible measures of lesion and enhancing lesion, with minimal or no user intervention. In contrast with previous algorithms, this method has been designed to be able to accurately quantify lesion and enhancing lesion membership even when no examples of frank lesion or enhancing lesion exist in the volume, for example, the algorithm performs supervised classification even when there are no examples. The method is relatively unaffected by changes in scanner and acquisition parameters.

Using the sample point generator, which identifies the white matter samples, the CSF samples, and the maximum enhancement automatically, the lesion detector has been shown to be highly reproducible, as well as automatic. The system provides an automatic and deterministic inhomogeneity correction, registration, and parenchyma mask generation. Although included in the detailed description below, these are in fact separate processes. When the processing pipeline uses deterministic sub-algorithms, the present change detection method yields consistent results every time it is run with the same volume data, regardless of who runs the application, where it is run, or how many times it is run.

Yet another aspect of the present invention is a method for comparing two MRI images of the head and identifying and characterizing changes that have occurred in white matter lesions that may be present. The method produces a color-coded change map, which is displayed superimposed upon the anatomical images. This color-coded change map identifies what has changed in the interval between the two MRI acquisitions, in what way, by how much, and where. The method aids in the accurate and simple identification of changes in serial brain MR images. The system provides a mechanism to ensure that all changes within serial MR images are observed and understood. The system provides a mechanism for defining progression, for example, with regard to brain tumors, objectively. The system provides a mechanism for quantitatively comparing response to trial therapies across treatment groups. The system additionally provides a mechanism to promote reproducible diagnoses. The system may help to train new practitioners. It may serve as a model for how computers can liberate radiologists from doing mundane things sub-optimally, for example, measuring tumors with rulers on plastic film, which has been shown to be relatively ineffective. Instead a computer wades through mountains of analyses and presents the clinician only with refined, concise, and note-worthy data that has been tailored to their purpose. The method is a model of how computers can perform a large number of analyses and bring to a clinician's attention things they weren't looking for, but that are nonetheless important. The method additionally serves as a model of "layered analyses" that are impractical or impossible without computer assistance.

Another aspect of the present invention is a method for the detection of regions of significance, which uses a strong spatial connectedness criteria, and a variable threshold that weighs a region's spatial extent against the values of a given region's constituent voxels, to identify objects in a manner that possesses much higher sensitivity and specificity compared with simpler methods of separating signal from noise, such as thresholding. Additionally, the method possesses a training step allowing the algorithm to generate a quantitative definition of significance without explicitly modeling the noise. The method is further able to identify objects made of up elements with intensities within the range of the background noise. It is able to identify such low-intensity objects of arbitrary shape, unlike methods that have used kernels of fixed size and shape. Exploration and identification of arbitrarily sized and shaped regions within a noisy background is potentially computationally intractable. The particular implementation described below makes the method tractable on mainstream computing hardware. As a component of a change detector system, this method has been applied to digital phantoms, and to serial MR scans of brain tumor patients, and it has shown very high accuracy, sensitivity, and specificity.

In accordance with another aspect of the invention, a system is provided for automatically generating sample points from a series of medical images and identifying a significant region. The system includes an image acquisition system configured to acquire the series of medical images of a region of interest (ROI) in a subject. An automated mask generator is included and configured to review the series of medical images and automatically generate a brain parenchyma mask, wherein the brain parenchyma mask is used to designate sample points. An automated sample point generator is configured to review the series of medical images and automatically detect portions of the series of medical images indicative of a material expected to be in the ROI and designate sample points therefrom using the brain parenchyma mask. In addition, a lesion identification system is configured to utilize the sample points to create a mathematical description of a lesion and an enhanced lesion within the series of medical images. A lesion change detection system is configured to detect a change in the mathematical description of the lesion within the series of medical images from a prior mathematical description of the lesion within a prior series of medical images. A significant region detector is also included to automatically identify a significant object in the series of medical images, wherein the significant region detector includes a training process that generates a quantitative definition of significance.

In accordance with yet another aspect of the invention, a system is provided for automatically generating sample points from a series of medical images and identifying a significant region. The system includes an automated sample point generator configured to review a series of medical images and automatically detect portions of the series of medical images indicative of a material expected to be in a ROI included in each of the series of medical images and designate sample points within the series of medical images therefrom. A lesion identification system is configured to utilize the sample points to create a mathematical description of a lesion and an enhanced lesion within the series of medical images. A lesion change detection system is configured to detect a change in the mathematical description of the lesion within the series of medical images from a prior mathematical description of the lesion within a prior series of medical images. The system includes a significant region detector to automatically identify a significant object in the series of medical images, wherein the significant region detector includes a training process that generates a quantitative definition of significance.

Another aspect of the invention is a method for automatically generating sample points from a series of medical images and identifying a significant region. The method includes acquiring a series of medical images of a region of interest (ROI) in a subject; automatically reviewing the series of medical images and automatically generating a brain parenchyma mask therefrom, and using the brain parenchyma mask for designating sample points; automatically reviewing the series of medical images and automatically detecting portions of the series of medical images indicative of a material expected to be in the ROI and designating sample points therefrom using the brain parenchyma mask; utilizing the sample points for creating a mathematical description of a lesion and an enhanced lesion within the series of medical images; detecting a change in the mathematical description of the lesion within the series of medical images from a prior mathematical description of the lesion within a prior series of medical images; and automatically identifying a significant region in the series of medical images.

This invention is based in part on the realization that there are situations where domain-specific knowledge exists that can be leveraged to identify regions of significance lower than the noise floor. This knowledge could take a variety of forms. For example, in the case outlined in this application, it is known a priori that the three dimensional (3D) object that the image represents, is a real-world object, for example, a patient's brain. Within this brain, various types of objects or regions exist. An example of such an object or region could be a region of T2 abnormal white matter, or a region which is exhibiting increasing, that is, changing, T2 abnormality. In such cases, high intensity, either in a lesion membership image, or in a change in lesion membership image, is only one trait signifying a particular voxel's membership or lack of membership in the object or region of interest. This is because the object might possess only subtle intensity relative to the background. However, in many such cases, it is known a priori that objects, including subtle objects, frequently extend to encompass the space of multiple or many voxels, and are more or less continuous over the region which they cover. The extent of the region might serve as a second piece of knowledge, suggesting its membership in the region, while the continuousness of the region, that is, the fact that it is not thin and winding, and it is not full of holes, may serve as a third piece of knowledge. These three pieces of knowledge constitute the foundation for separating objects from background noise.

Various other features of the present invention will be made apparent from the following detailed description and the drawings.

DESCRIPTION OF THE PREFERRED EMBODIMENT

This invention is described in preferred embodiments in the following description with reference to the figures in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment,' "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flowcharts included are generally set forth as logical flowchart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
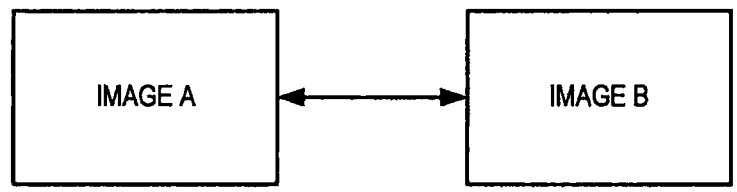
FIG. 1 is an exemplary block diagram of a typical prior art image comparison.
Figure 2:
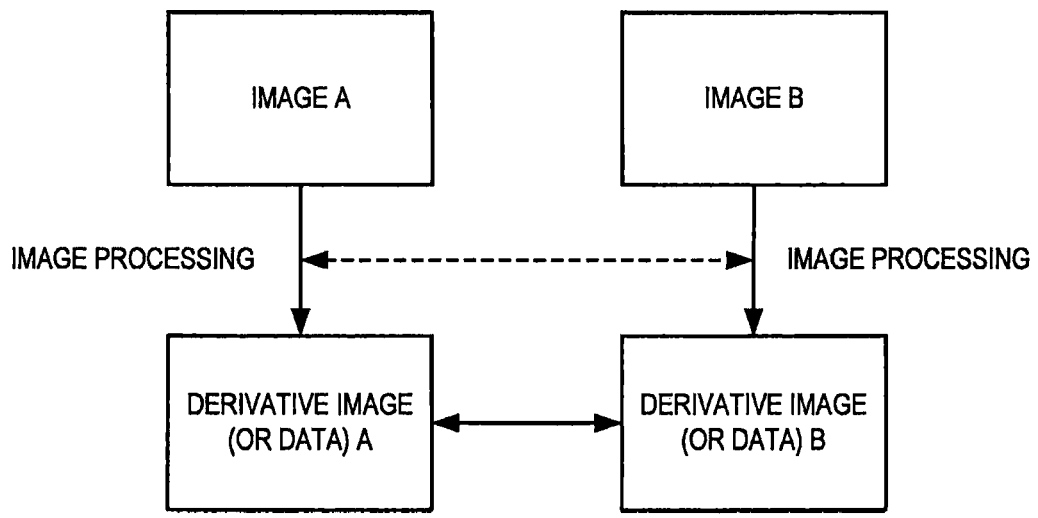
FIG. 2 is an exemplary block diagram of a more sophisticated prior art image comparison method.
Figure 3:
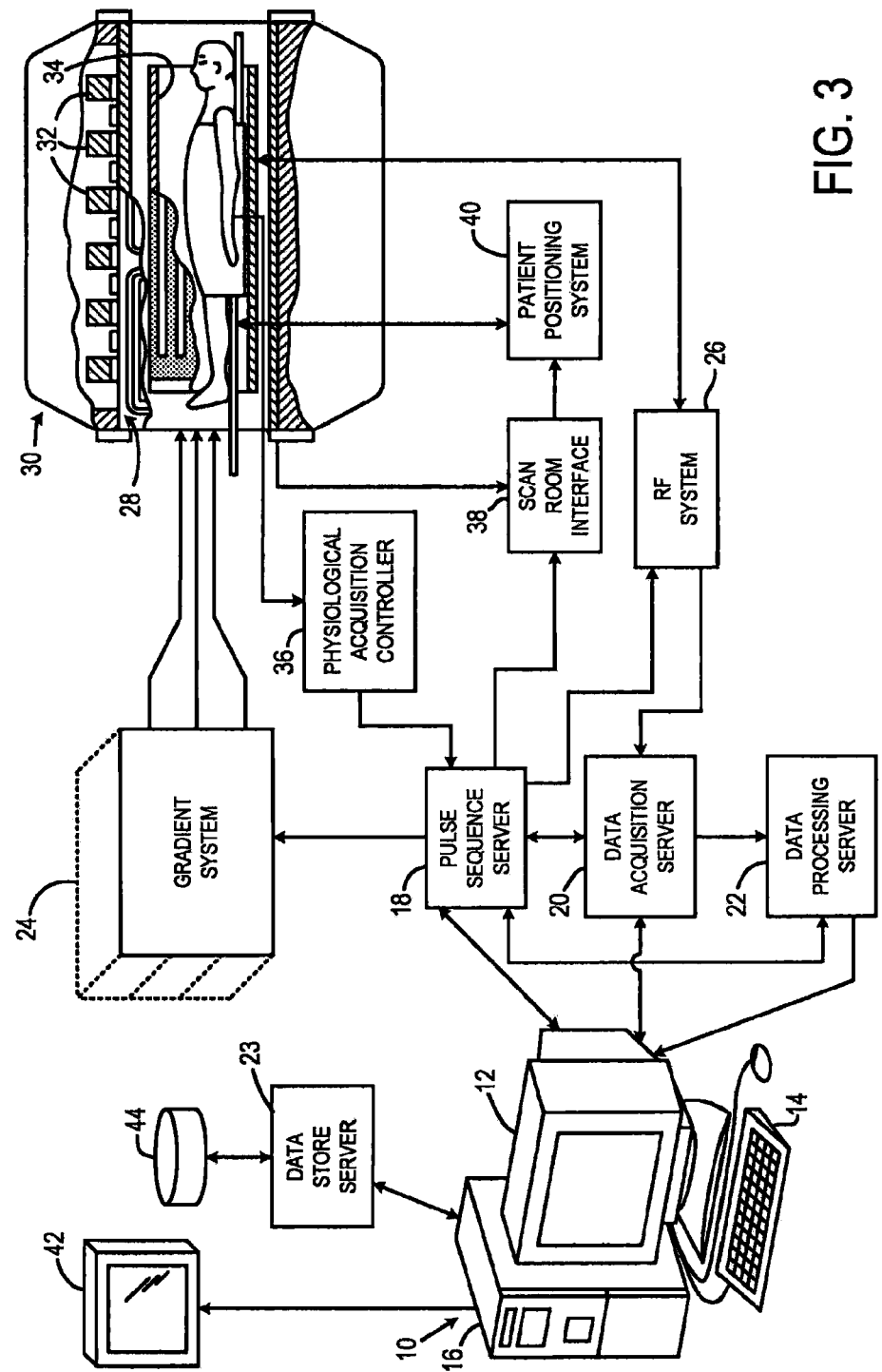
FIG. 3 is an exemplary block diagram of an MRI system which employs the present invention.

Turning to FIG. 3, the one embodiment is employed in a magnetic resonance imaging (MRI) system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system.

The workstation 10 is coupled to four servers. Specifically, the work station 10 includes a pulse sequence server 18; a data acquisition server 20; a data processing server 22, and a data store server 23. In one embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network. This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding nuclear magnetic resonance (NMR) signals. The gradient coil assembly 28 forms part of a magnet assembly 30 that includes a polarizing magnet 32 and a whole-body radio frequency (RF) coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector that detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1}Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs that receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans that require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information that is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 4:
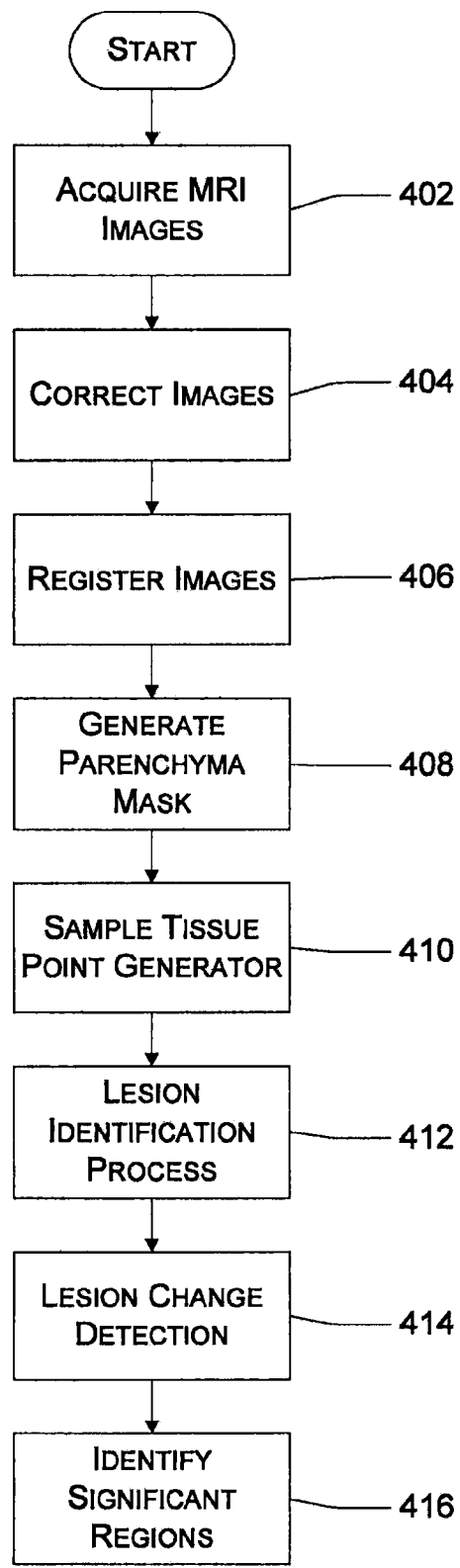
FIG. 4 is an exemplary flowchart of the major elements in the one embodiment of a brain lesion change detector system.

Referring particularly to FIG. 4, one method according to the present discussion employs the above-described MRI system to acquire a number of images from a subject's brain as indicated at block 402. These three dimensional (3D) images are also referred to herein as "volumes."

After the images have been acquired, intensity inhomogeneities are generally still present in the images. Thus, each volume acquired is first processed using a third-party inhomogeneity correction algorithm as indicated at block 404. For example, N3 may be used, but other solutions may be used, as well.

As indicated at block 406, the volumes are spatially registered to one another to establish a common spatial framework. In accordance with one aspect of the invention a proprietary solution may be used that is a hybrid of other third-party registration algorithms. Registration should be as fine as possible, preferably sub-voxel, and should be capable of tolerating changes over time. In some embodiments, registration may be done in an all-to-one fashion, in order to avoid cumulative errors.

A brain parenchyma mask is then generated as indicated by block 408. The structure and process of generating the parenchyma mask will be described in detail below in conjunction with FIGS. 5 and 6.

As indicated at block 410, the tissue sample generator is then employed to produce from the acquired image volumes sample pixel values for white matter, gray matter, and cerebrospinal fluid (CSF). In addition, it finds the maximum enhancement level produced in the images by an administered contrast agent. The structure and operation of the tissue sample point generator is described in detail below in conjunction with FIGS. 7-11.

As indicated in FIG. 4, at block 412, a lesion identification process is then performed. This employs the acquired image volumes and the calculated tissue samples to locate and quantify any abnormal tissues. The structure and operation of the lesion identification process is described in detail below in conjunction with FIGS. 12-17.

Next, as indicated at block 414, the next step is to detect changes that have occurred in identified lesions since the last examination. The process 414 accomplishes this by comparing the current identified lesions with lesions identified in previous examinations that have been stored for this purpose. The operation and structure of the lesion change detector is described in detail below in conjunction with FIG. 18.

And finally, as indicated at block 416, the last step is to identify significant regions by distinguishing objects from background noise in images. The operation and structure of the identification of significant regions is described in detail below in conjunction with FIGS. 19-23.

In certain embodiments, individual steps recited in FIG. 4 may be combined, eliminated, or reordered. In other embodiments, instructions, such as instructions provided in FIG. 4, may reside in computer readable medium wherein those instructions are executed by a processor to perform one or more of processes recited in FIG. 4. In still other embodiments, the instructions may reside in any other computer program product, where those instructions are executed by a computer external to, or internal to, data storage system, to perform one or more of steps recited in FIG. 4. In either case, the instructions may be encoded in computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compact-flash, smartmedia, and the like.

Mask Generation

Figure 5:
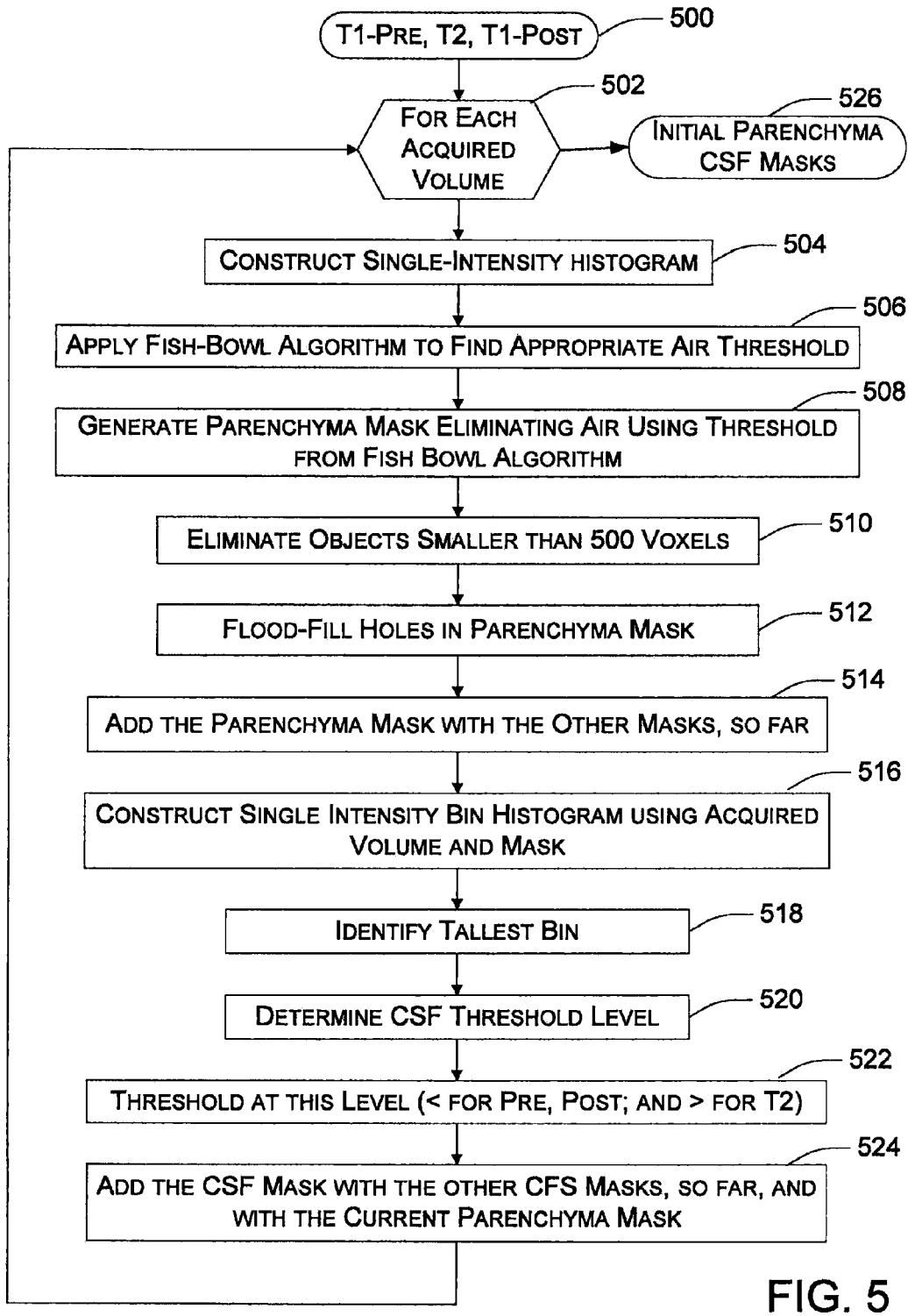
FIG. 5 is an exemplary flowchart for generating the initial brain parenchyma and CSF mask.

FIG. 5 illustrates an exemplary flowchart for generating the initial brain parenchyma and CSF mask, both of which are subsequently used to generate tissue sample points. As will be understood by an individual of ordinary skill in the art, the automatic generation of the parenchyma mask is an advancement over prior methods wherein the user had to supply a separately generated parenchyma mask. In particular, the user is, therefore, not required to specify which image regions are completely defined in all processes.

As shown in resource block 500, the method uses T1-Pre, T2, and optionally T1-Post volumes. As is understood by one of ordinary skill in the art, the term "T1" refers to T1 relaxation time, also referred to as spin lattice or longitudinal relaxation time. Specifically, T1 refers to the time period for proton spins to experience longitudinal magnetization recovery following excitation. This longitudinal relaxation is due to energy exchange between the spins and surrounding lattice re-establishing equilibrium. Similarly, the term "T2" refers to T2 relaxation time. Specifically, T2 refers to the time period for proton spins to experience transverse magnetization recovery following excitation. This transverse relaxation results from spins getting out of phase and, as the spins move together, their individual magnetic fields interact to slightly modifying their precession rate, thus, causing a cumulative loss in phase resulting in transverse magnetization decay. Further, the terms "pre" and "post" refer to pre and post injection of a contrast agent.

For each T1-Pre, T2, and, optionally, T1-Post volume acquired, as indicated by block 502, a single-intensity histogram is constructed at process block 504. As used in this discussion, the term "single-intensity histogram" is used refer to a histogram, where each bin corresponds to one discrete intensity in the given image.

A fish-bowl algorithm is then applied to find the appropriate air threshold at block 506. The fish-bowl algorithm may be specifically limited to examining intensities greater than ten (10) units to avoid low-intensity histogram spikes resulting from thresholding. The specific details of the this algorithm will be subsequently discussed in conjunction with FIG. 6.

Once the air threshold has been determined, an initial parenchyma mask is generated by eliminating air using the thresholds provided by the fish-bowl algorithm, as indicated in block 508. Next, objects smaller than 500 voxels are eliminated from the initial parenchyma mask and holes are flood-filled, as indicated by blocks 510 and 512 respectively. As the process is iterative, the just generated parenchyma mask is then added to the other parenchyma masks, if any, generated thus far using the other acquired volumes, as indicated in block 514.

To generate the CSF mask, as indicated by block 516, a single intensity bin histogram is then created using the acquired volume and resulting mask from block 514. The tallest bin is then identified, as indicated by blocks 518. Next, as seen by block 520, the CSF threshold level is determined. This is done by walking the histogram from the tallest bin until the level drops to half the peak height. Where the acquired volume is T1-Pre or T1-Post, the histogram is walked to the right. Otherwise, if T2, the histogram is walked to the left. As indicated by block 522, the CSF mask is then generated by using the threshold at this level. Finally, as with the parenchyma mask, the CSF mask is then added to the other CSF masks, if any, generated thus far using the other acquired volumes, as indicated in block 524.

Once done, the next acquired volume is selected at block 502, and blocks 504 through 524 are repeated. When each acquired volume has been processed, the resulting output are the initial parenchyma and CSF masks, as indicated by resource block 526, which may be then used in the tissue sample generating algorithms.

Figure 6:
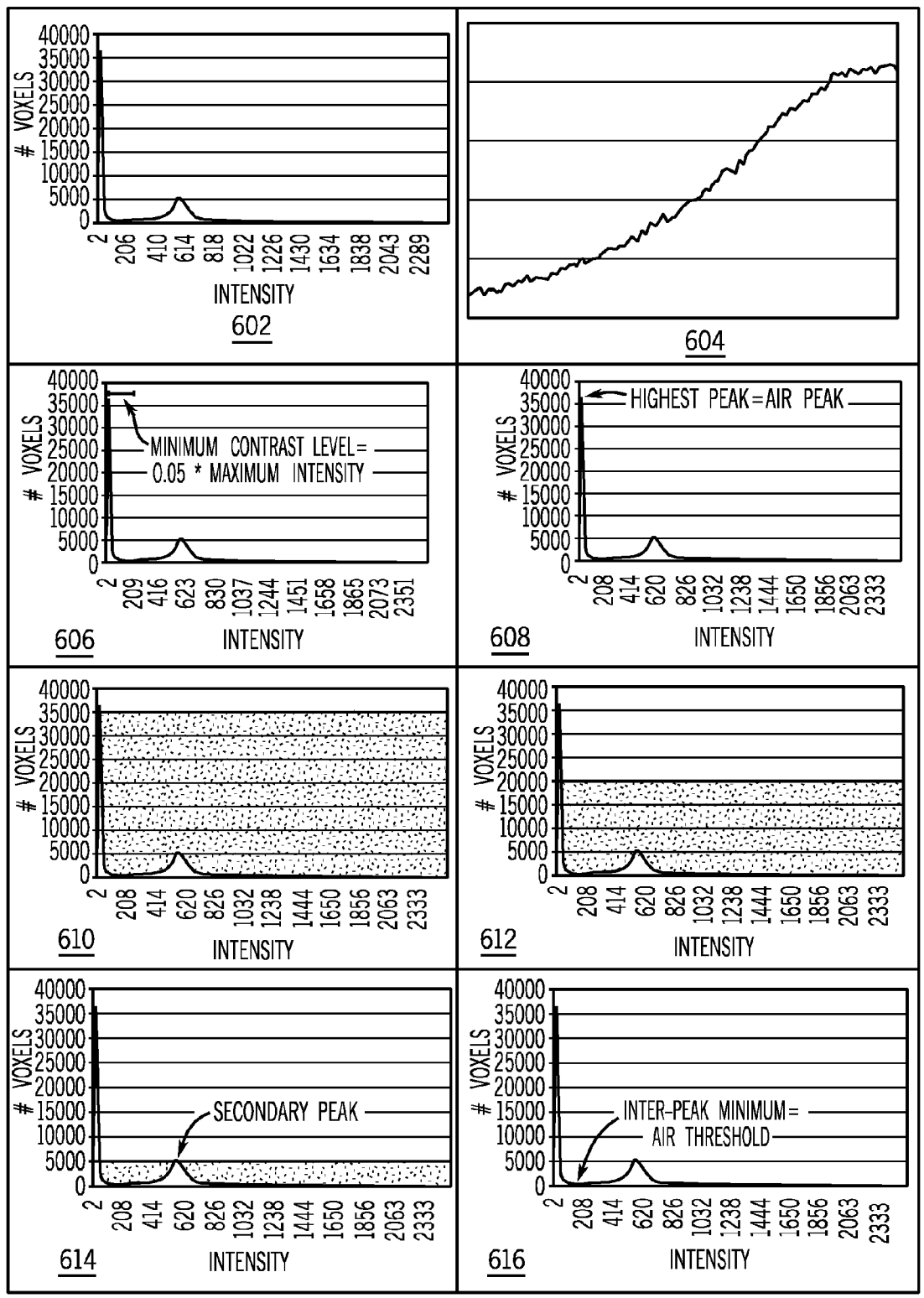
FIG. 6 is an exemplary set of data sets used with the fish-bowl algorithm described with respect to FIG. 5 to generate the initial brain parenchyma and CSF mask.

Referring now to FIG. 6, the fish-bowl algorithm is illustrated by way of a series of data sets. Specifically, the fish-bowl algorithm is the initial processing applied to a histogram from an acquired image (here, a T1-Post image) in order to identify the air peak, the secondary peak, and the upper air threshold. The technique applies a priori knowledge, in conjunction with a watershed algorithm. As will be known to those of ordinary skill in the art, a watershed algorithm is a known image processing segmentation algorithm that splits images into areas, based on the topology of the image.

First, a histogram is constructed from the intensities in the image, as shown in 602. Note that some imaging systems pad the exterior margins of the image with single valued voxels (e.g. voxels with an intensity of 0). These single-valued margins induce extremely tall spikes in the histogram. In 602, these single-valued margins have been removed, simply by thresholding at an intensity of ten (10) units (the assumption being that the tall part of the air distribution extends greatly above an intensity of ten (10) units). In order to apply the fish-bowl algorithm, any such single valued patted margins should be removed, so that no spikes are present in the histogram.

Within the histogram shown in 602, each bin corresponds to one discrete intensity from the image. This one intensity bin approach, results in a very jagged histogram, as can be seen in 604, which depicts a zoomed in version of the left-half of the secondary peak from 602. The jaggedness of the histogram means that the curves are far from monotonic, and results in some ambiguity regarding what constitutes a 'secondary peak.' Therefore, as shown in 606, a 'minimum contrast level' is established at 0.05 times the maximum intensity of the image. This minimum contrast level is designed to reliably overcome the jaggedness of the histogram. That is, by taking the view that no matter how jagged a particular histogram is, a bin this far to the right of a bin in the air distribution will never be higher than the bin in the air distribution, due only to jaggedness. In other words, over the scale of the minimum contrast level, the primary peak is monotonic.

As shown in 608, the highest peak in the histogram is chosen as the air peak. A watershed algorithm is commenced, with the water level set to the height of the air peak bin, as illustrated by the grey area of 610. The water level is lowered, as indicated by 612, until a second peak appears, as indicated by 614. This second peak is at least the minimum contrast level from the air distribution and corresponds to grey matter (and usually white matter and CSF, as well). The algorithm finally searches between the primary and secondary peaks for the lowest point between these two peaks, and selects this point as the upper threshold intensity for air, as illustrated by 616.

In certain embodiments, individual steps recited in FIGS. 5 and 6 may be combined, eliminated, or reordered. In other embodiments, instructions, such as instructions provided in FIGS. 5 and 6, may reside in computer readable medium wherein those instructions are executed by a processor to perform one or more of processes recited in FIGS. 5 and 6. In still other embodiments, the instructions may reside in any other computer program product, where those instructions are executed by a computer external to, or internal to, data storage system, to perform one or more of steps recited in FIGS. 5 and 6. In either case, the instructions may be encoded in computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

Tissue Sample Point Generator

Figure 7:
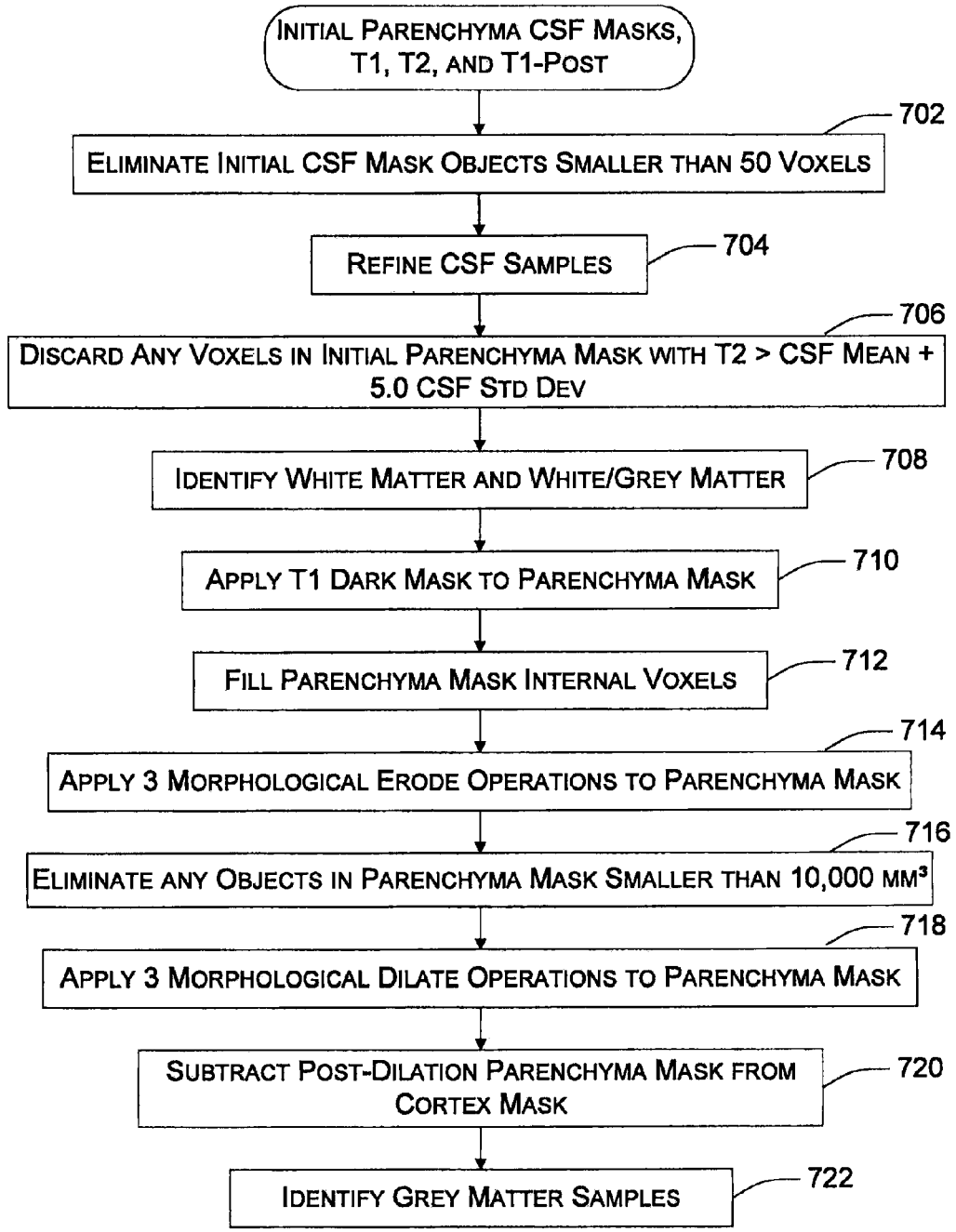
FIG. 7 is an exemplary high-level flowchart illustrating the process of generating tissue sample points.

FIG. 7 shows a high level flowchart for determining sample points. As shown in resource block 700, the method uses initial brain parenchyma and CSF masks generated from T1-Pre, T2, and optionally, T1-Post images using the exemplary process illustrated in FIG. 5. Additionally resource block 700 includes T1, T2, and, optionally, T1-Post images. The process depicted in FIG. 7 first finds CSF samples and uses the samples in the process to identify white and white/grey, and finally grey matter sample points.

As will be understood by a person of ordinary skill in the art, the ability to generate sample points is an advancement over the prior art. Typically, sample points have been supplied by the user for, for example, grey matter, white matter, and CSF. This requires both time and a reasonably high degree of expertise and introduces inter and intra-observer variability. Also, as will be clear to a person of ordinary skill, the exemplary process described in FIG. 7 overcomes this by deriving the sample points automatically reproducibly.

Further, whereas previous automated algorithms were able to generate samples of lesions and enhancement of tissue types, the exemplary process described in FIG. 7 additionally generates samples of normal appearing white matter (NAWM), grey matter, and CSF. As will be clear to one of ordinary skill in the art, the exemplary process described in FIG. 7 is more robust against metal artifacts or large deviations from normal anatomy (e.g., large surgical resections). Further, this process does not require that the user supply a separately generated parenchyma mask because the parenchyma mask is instead automatically generated by the exemplary processes described in FIGS. 5 and 6. Thus, the process described in FIG. 7 is quite different from previously known methods.

Turning now to FIG. 7, first, objects smaller than, for example, 50 voxels are eliminated from the initial CSF mask, as indicated in block 702. Next, as shown by block 704, the CSF samples are refined. The details of refining the CSF samples are subsequently discussed in reference to FIG. 8. Once done, voxels in the initial parenchyma mask with T2 greater then the mean CSF value plus, for example, five (5) times the CSF standard deviation are discarded, as indicated in block 706.

The white matter and white/grey matter can then be identified, as shown by block 708. The process of making such an identification, including the generating of white/grey matter, T1 white matter, and T1 darker matter masks, is discussed in detail below in connection with FIG. 10. Next, at block 710, the T1 darker matter mask is applied to the parenchyma mask, and, at block 712 the internal voxels of the parenchyma mask are filled.

At block 714, three (3) morphological erode operations are applied to the parenchyma mask. As will be understood by one of ordinary skill in the art, morphological erosion is a mathematical process of eroding away the boundaries of foreground pixels, resulting in the area of the foreground pixels decreasing in size, and any holes within those areas becoming larger. Once done, any objects in the parenchyma mask smaller than, for example, 10,000 mm$^3$ are eliminated at process block 716. The resulting mask is referred to as the cortex mask.

Next, at block 718, three (3) morphological dilate operations are applied to the parenchyma mask, the result being a post-parenchyma mask. Similar to the morphological erode operations, a person of ordinary skill in the art will know that a morphological dilation is a mathematical process whereby the areas around foreground pixels are enlarged at their boarders, resulting in the foreground pixels growing in size, while background holes shrink.

At block 720, the post-dilation parenchyma mask is subtracted from the cortex mask. Finally, as indicated by block 722, grey matter samples can be identified. The specific details of identifying the grey matter will be subsequently discussed in conjunction with FIG. 11.

As will be understood by those of ordinary skill in the art, the exemplary process illustrated by FIG. 7 takes either two or three pulse sequences, upon which the automated sample points and automated parenchyma mask generation algorithms are based and can be extended such that it derives sample points for additional pulse sequences, such as fluid-attenuated inversion recovery (FLAIR) and proton density (PD). It will also be understood by a person of ordinary skill in the art, that since the coordinates of the CSF samples are based on T1 and T2, CSF samples in FLAIR would be correct and unaffected by FLAIR fluid suppression artifacts.

Figure 8:
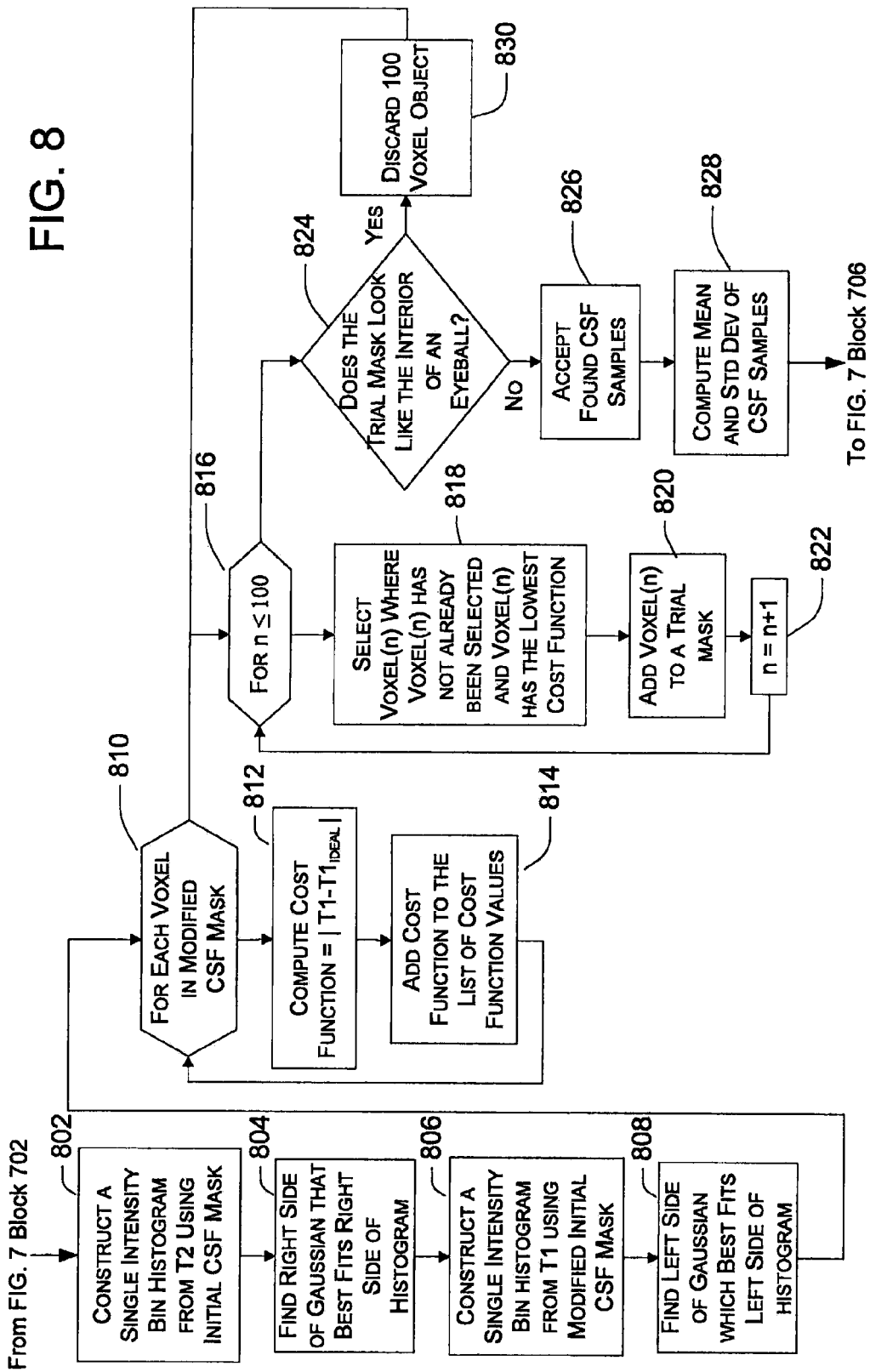
FIG. 8 is an exemplary flowchart depicting the process of refining CSF samples.

Turning to FIG. 8, and exemplary flowchart depicting the process of refining CSF samples is illustrated. To start, at block 802 a single intensity bin histogram is constructed from the T2 image using the initial CSF mask created by the process described in FIG. 5. Next, at block 804, the best fit of the right side of a Gaussian distribution curve to the right side of the histogram is determined. Excluded from the initial CSF mask are all voxels with T2 intensities less than the Gaussian center less 4.0σ.

A second single intensity bin histogram is constructed from T1 using the now modified initial CSF mask, at block 806. At block 808, the best fit of the left side of a Gaussian distribution curve to the left side of the histogram of block 806 is determined. The value $T1_{ideal}$ equals the center of this best fit Gaussian.

Next, as indicated by block 810, for each voxel in the modified CSF mask, the cost function is determined and added to a list of cost function values, as indicated by blocks 812 and 814 respectively. The cost function is equal to $T1-T1_{ideal}$.

Next, an iterative loop begins at block 816 for n less than or equal to 100, where n is initially set to unity. At block 818, the voxel(n) is selected, where voxel(n) has the lowest cost function value and has not previously been selected. Voxel(n) is then added to a trial mask and n is incremented by unity, at blocks 820 and 822 respectively.

Where n is less than or equal to 100, at block 816, then blocks 818 through 822 are repeated. When n is greater than 100, the trial mask, now a 100 voxel object, is examined to determine if it looks like the interior of the eyeball, as indicated by decision block 824. The process of this examination will be discussed in greater detail in conjunction with FIG. 9. If not, then the voxels are accepted as the CSF samples and the mean value and standard deviation of the CSF samples are determined, as indicated by blocks 826 and 828 respectively. If the trial mask does look like the interior of an eyeball, then the voxels comprising the trial mask are discarded at block 830 and blocks 816 through 822 are repeated.

Figure 9:
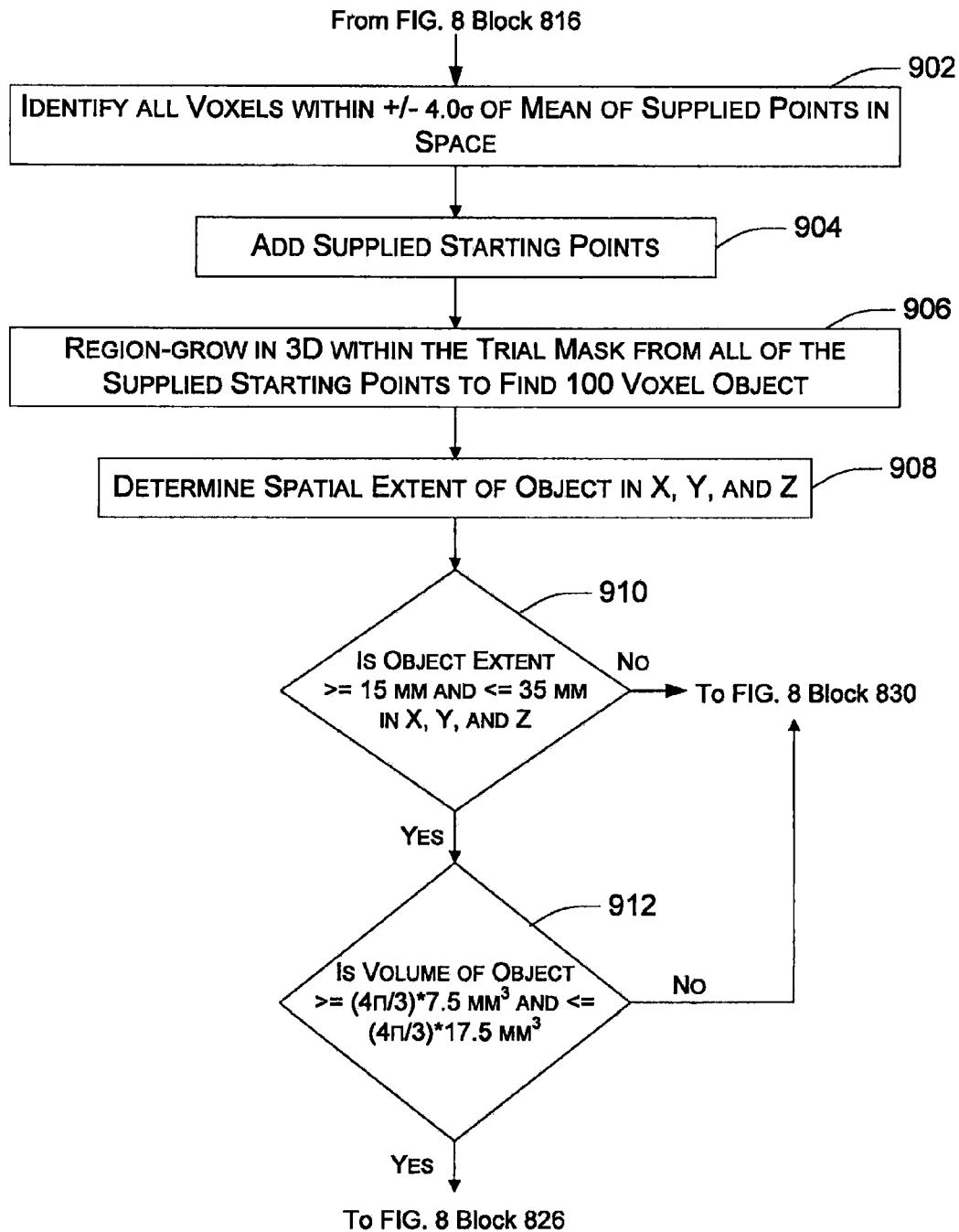
FIG. 9 is an exemplary flowchart depicting a process of determining whether the 100 voxel object created in FIG. 8 corresponds to CSF or the vitreous humor of the eye.

FIG. 9 presents and exemplary flowchart depicting a process of determining whether the 100 voxel object correspond to CSF or vitreous humor of the eye. To begin, at block 902, all voxels within plus or minus 4.0σ of the mean value of the supplied points in T1-Pre and T2 space are identified and, at block 904, are supplied as starting points. As indicated in block 906, the supplied starting points within the trial mask are region-grown in 3D to find the 100 voxel object in question. As is well known by one of ordinary skilled in the art, region growing is a standard mathematical process for manipulating voxels. Next, the spatial extent of the 100 voxel object in X, Y, and Z is determined at block 908.

First, the extent of the 100 voxel object is examined in decision block 910. If the extent of the 100 voxel object is greater then or equal to 15 mm but less than or equal to 35 mm in X, Y, and Z, then the volume of the 100 voxel object is examined in decision block 912. Where the extent falls outside these ranges, the process is returned to block 830 of FIG. 8, the 100 voxel object being discarded. As indicated by decision block 912, if the volume of the 100 voxel object is greater than $4\pi/3$ times $7.5 \text{ mm}^3$ but less than or equal to $4\pi/3$ times $17.5 \text{ mm}^3$, then the process is returned to block 826 of FIG. 8, the CSF samples being accepted. If not, then the process is returned to block 830 of FIG. 8, the 100 voxel object being discarded.

Figure 10:
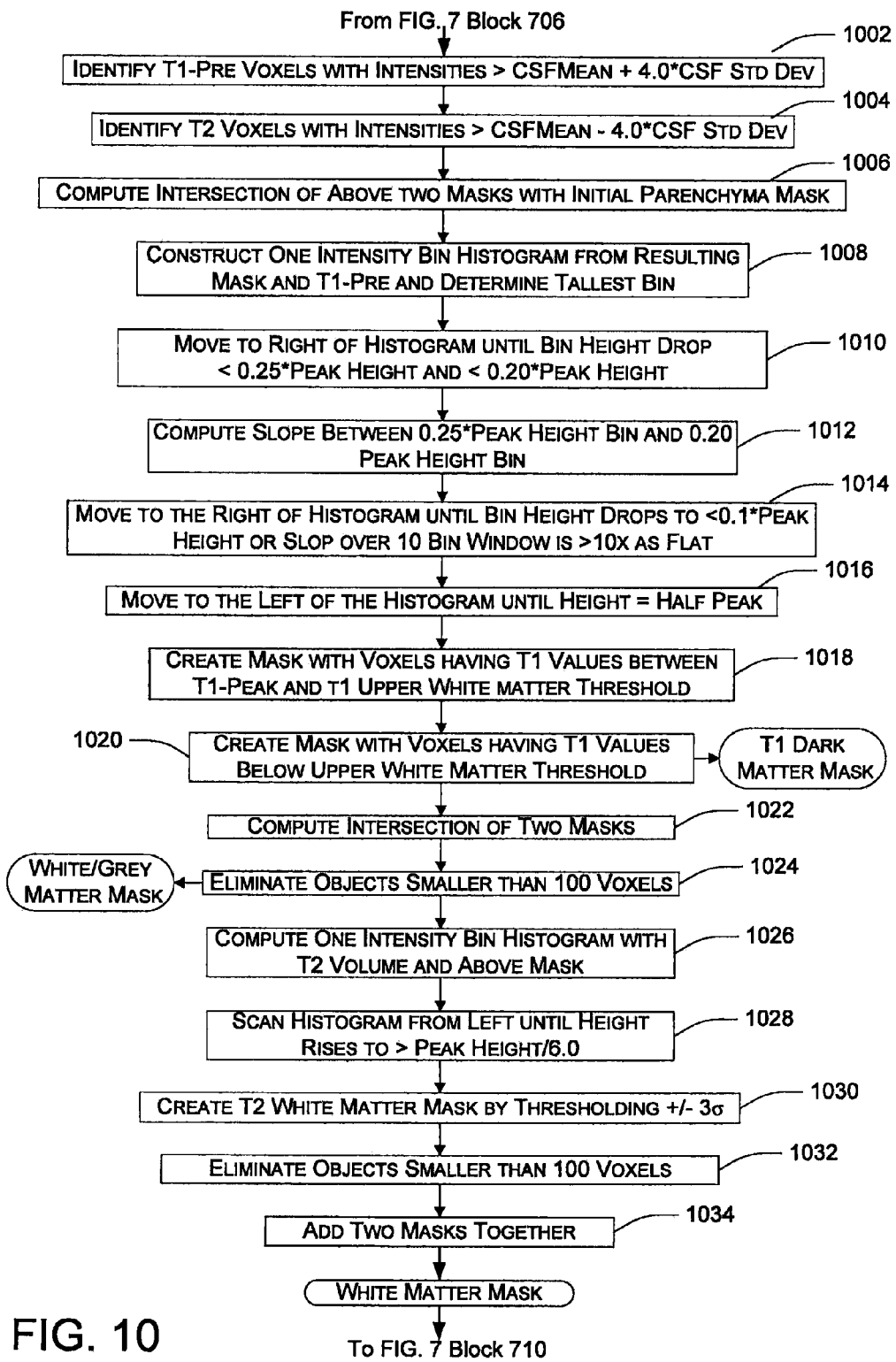
FIG. 10 is an exemplary flowchart depicting a process of identifying white matter and white grey matter.

Referring now to FIG. 10, a flowchart is presented depicting an exemplary process of identifying white matter and white grey matter, the process resulting in the creation of white/gray matter, white matter, T1 dark matter masks. To start, T1-Pre voxels with intensities greater than the mean CSF plus, for example, four (4) times the CSF standard deviation are identified, as indicated in block 1002. Next, T2 voxels with intensities greater than the mean CSF minus, for example, 4.0 times the CSF standard deviation are also identified. The intersection of the masks created in blocks 1002 and 1004 with the initial parenchyma mask is then computed, as indicated in block 1006.

A one intensity bin histogram is then constructed from the mask resulting from block 1006 and the T1-Pre image and the tallest bin is determined, as seen in block 1008. Next, as indicated by block 1010, the intensity of the voxel is determined where the bin height drops to less than one-quarter of the peak height when the histogram is walked to the right. The intensity of the voxel is also determined where the bin height drops to one-fifth of the peak height when the histogram is walked to the right. The slope is then determined between the bin at one-quarter of the peak height and the bin at one-fifth the peak height, as indicated by block 1012. The histogram is further walked to the right until either the bin height drops to less than one-tenth the peak height or the slope over a ten (10) bin window becomes more then ten (10) times as flat, as indicated in block 1014. The intensity of the voxel at this point is denoted as the T1 upper white matter threshold.

Next, as seen in block 1016, the histogram is walked from the peak to the left until the height drops to one-half the peak height. A mask is then created with the voxels having T1 values between the T1 peak value and the T1 upper white matter threshold and another with voxels having T1 values below the T1 upper white matter threshold, as indicated by blocks 1018 and 1020. The mask created in block 1020 is also known as the T1 darker mask and is used in block 710 of FIG. 7. The intersection of the masks created in blocks 1018 and 1020 is then determined and all objects smaller than 100 voxels are eliminated, as indicated by blocks 1022 and 1024. The resulting mask is identified as the white/grey matter mask.

At block 1026, a one intensity bin histogram is computed with the T2 volume and the mask created in block 1024. The histogram is then scanned from the left until the height is greater than one-sixth the peak height, as indicated in block 1028. The T2 white matter mask is then created by thresholding from the point determined in block 1028 plus or minus 3.0σ, as indicated in block 1030. Objects smaller than 100 voxels are then eliminated, as indicated in block 1032. The white/grey matter mask is then added to the T2 white matter mask, as indicated by block 1034, resulting in the white matter mask.

Figure 11A:
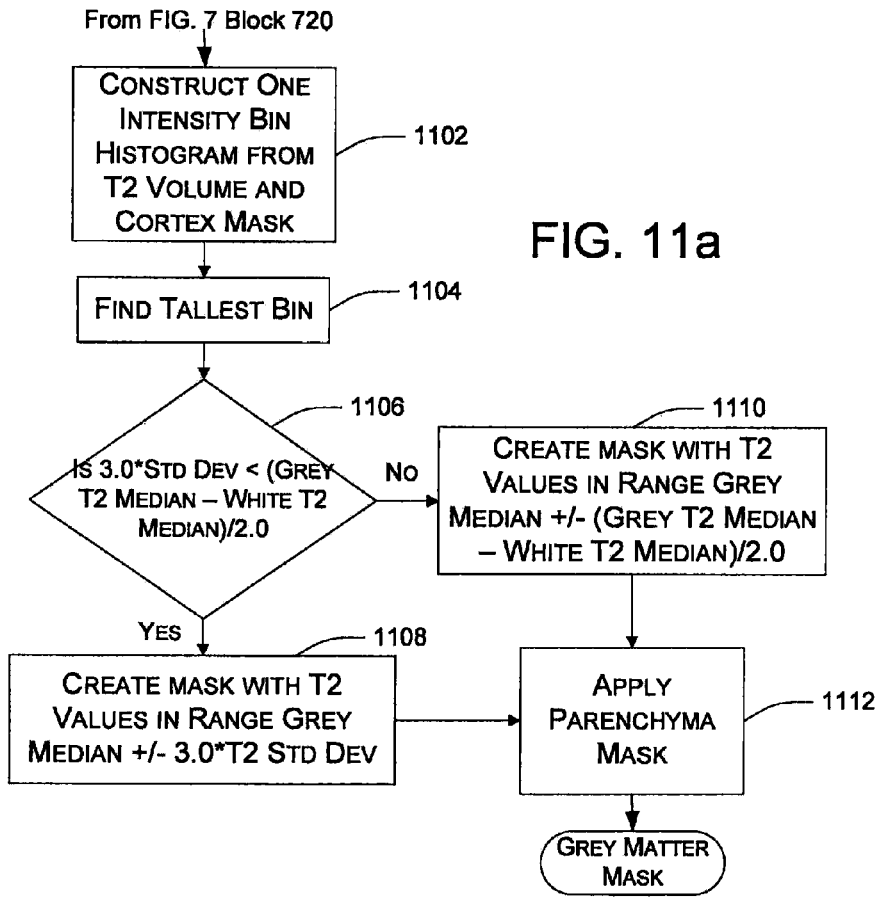
FIGS. 11a-11c present exemplary flowcharts depicting a process of identifying grey matter samples.
Figure 11B:
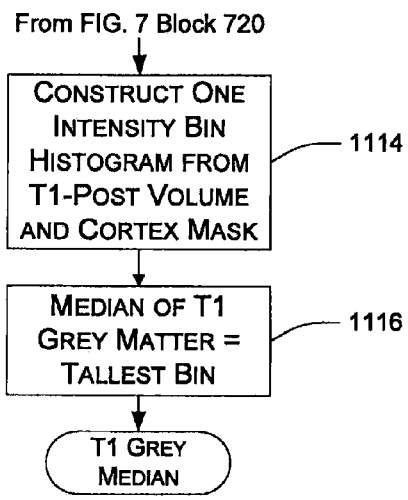
Figure 11C:
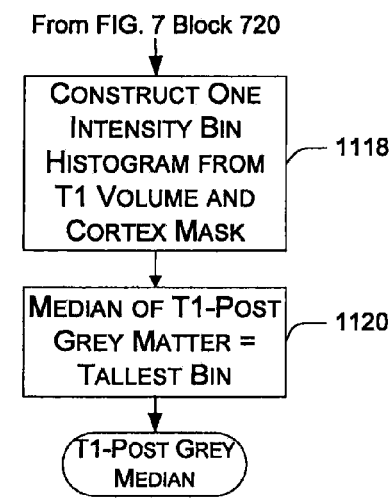

Referring now to FIGS. 11a-11c, an exemplary process of identifying grey matter samples is presented, the process resulting in creating a grey matter mask, as well as identifying the gray T1 median, gray T1-post median, and grey T2 median. In generating the grey matter mask, a one intensity bin histogram is constructed from the T2 volume and cortex mask, as indicated in block 1102. The tallest bin on this histogram is then identified, as indicated by block 1104, and represents the T2 gray matter medium.

Next, if three times the T2 standard deviation is less than one-half the T2 grey matter median less the T2 white matter median, then a mask is created with T2 values in the range of the T2 grey matter median plus or minus three times the T2 standard deviation, as indicated in block 1108. Otherwise, as indicated in block 1110, a mask is created with T2 values in the range of the T2 grey matter median plus or minus one half of the T2 gray matter median less the T2 white matter median. The resulting mask is then, in block 1112, applied to the parenchyma mask, resulting in the grey matter mask.

The T1 grey matter median is determined by constructing a one intensity bin histogram from the T1 volume and cortex mask, as indicated in block 1114. The T1 grey matter median equals the tallest bin, as shown by block 1116.

Similarly, the T1-post grey matter median is determined by constructing a one intensity bin histogram from the T1-post volume and cortex mask, as indicated in block 1118. The T1-post grey matter median equals the tallest bin, as shown by block 1120.

As will be understood by one of ordinary skill in the art, the automated sample points algorithm discussed herein and illustrated by FIGS. 7-11 is based on a mathematical model for partial character (e.g., the tissue sampled using the MRI system described is a mix of tissue types in the same location) and partial volume (e.g., there are at least two different tissues or tissues mixes within the voxel, regardless of the size of the voxel). The presentation of partial-volume effects is consistent with a linear combination model, in which, if the voxel is known to contain fractions of exactly two tissues, when the position of the voxel is projected onto a line connecting the multispectral centroids of two constituent tissues, the fractional composition of the voxel can be implied. Thus, for example, a voxel containing gray matter and CSF laying half-way between the gray matter and CSF centroids in T1-T2 space, would be known to have half of its volume filled with gray matter, and the other half of its volume filled with CSF. Likewise, such a voxel lying three quarters of the way towards the CSF centroid from the NAWM centroid, would be assumed to contain 75% CSF and 25% NAWM by volume. The relationship between position on the line and membership is provided by the equation:

$$membership_A = \frac{|x - \mu_B|}{\mu_A - \mu_B}, membership_B = \frac{|x - \mu_A|}{\mu_A - \mu_B}$$

where membership$_A$ and membership$_B$ refer to the sample point's membership into a class of tissue, x is the intensity of the voxel whose membership in the two tissues is to be computed, $\mu_A$ is the mean intensity of the first tissue making up the partial membership line, and $\mu_B$ is the mean intensity of the second tissue making up the partial membership line.

The automated sample points generator provides input to the lesion finder and change detector algorithms described below. Certainly there are many other procedures that either use or could benefit from automatic sample point generation. One example is classification algorithms. Other less obvious examples include registration, inhomogeneity correction, anatomical atlas based segmentation, finite element model development, and the like. Particularly since the present method uses a priori knowledge that is as limited as possible, it should find application very early in any processing pipeline, and thus can serve as an important source of knowledge for other subsequent, higher-level stages of processing.

In certain embodiments, individual steps recited in FIGS. 7-11 may be combined, eliminated, or reordered. In other embodiments, instructions, such as instructions provided in FIGS. 7-11, may reside in computer readable medium wherein those instructions are executed by a processor to perform one or more of processes recited in FIGS. 7-11. In still other embodiments, the instructions may reside in any other computer program product, where those instructions are executed by a computer external to, or internal to, data storage system, to perform one or more of steps recited in FIGS. 7-11. In either case, the instructions may be encoded in computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

Lesion Identification

The lesion identification process uses the sample points automatically generated by the exemplary process described in FIGS. 7-11 to create a mathematical description of a lesion and enhance lesion imaging properties in the particular images.

Figure 12:
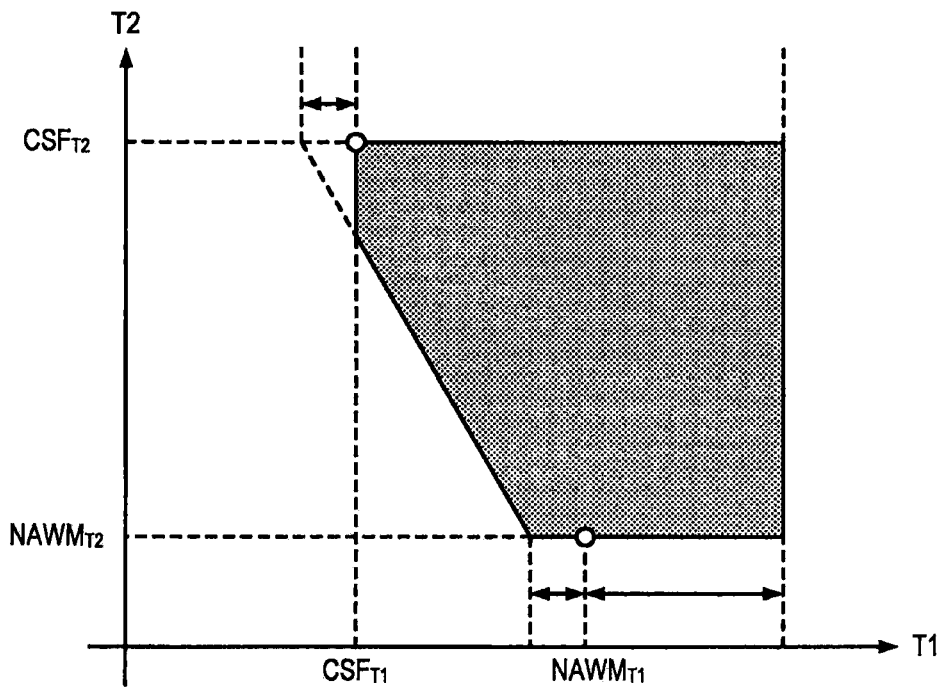
FIGS. 12 and 13 are exemplary charts illustrating a method of computing T1-T2 abnormality.
Figure 13:
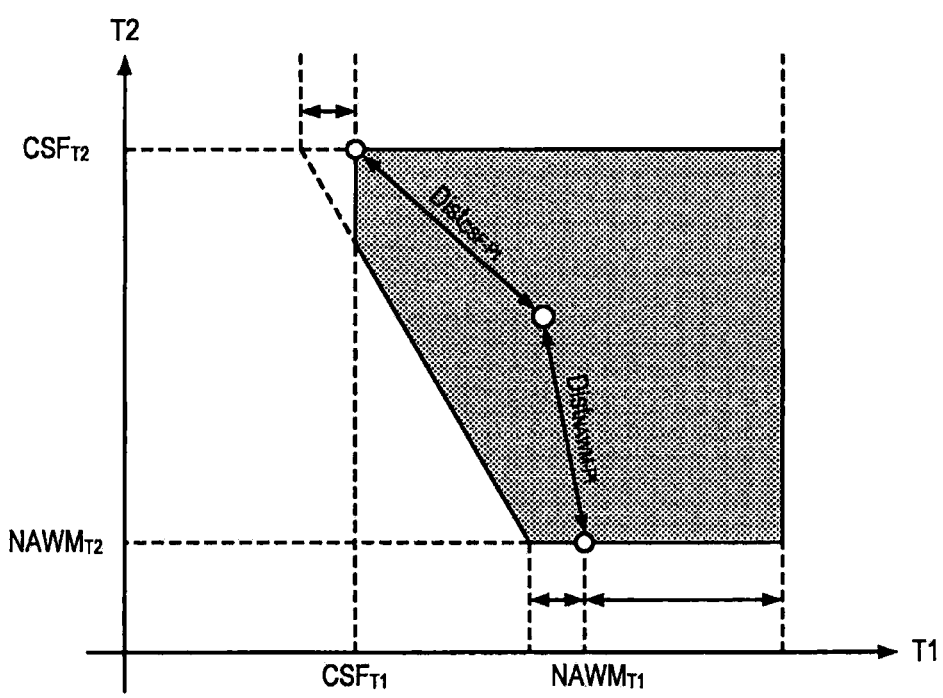

Turning first to FIGS. 12 and 13, the method used to compute T1-T2 abnormality can be explained. This step is first premised upon the observation that T1, for example, T1-hypointensity and T2, for example, T2 hyperintensity are exhibited in unison. Second, it is premised on the fact that T1-T2 abnormal white matter transitions in such a way that the more abnormal it becomes, the more its T1-T2 profile comes to resemble the T1-T2 profile of CSF. In some cases, the tissue first acquires T2 hyperintensity and only after it has acquired some degree of T2 hyperintensity does it begin to acquire T1 hypointensity and T2 hyperintensity concurrently. In other cases, the tissue acquires T1 hypointensity and T2 hyperintensity at the same time, from the first stages of abnormality acquisition. In all cases, white matter in all stages of normality and abnormality may be seen to exhibit T1-T2 profiles within the gray polygon shown in FIG. 12. In this figure, the location of the NAWM and CSF centroids are indicated by small circles. Ideally, the T1-T2 profile of abnormal white matter would lie within the portion of this polygon to the left of the NAWM centroid, however, blood can elevate the T1 value of white matter voxels in some cases and cause them to lie within the region of the polygon to the right of the NAWM centroid. The method first identifies the voxels which lie within the polygon. The method then computes the Euclidean distance of each such voxel in T1-T2 feature space from the NAWM and CSF centroids, as shown in FIG. 13. Finally, the method uses these distances to compute the membership of the voxels in the class "lesion" using the following equation:

$$membership_{lesion} = \frac{Dist_{PtToNAWM}}{Dist_{PtToCSF} + Dist_{PtToNAWM}}. \qquad (2)$$

This method uses the automatically determined sample points to normalize the intensities, which provides a high degree of robustness against changes in acquisition parameters, scanner, and the like. The memberships computed are therefore quantitative, and reproducible. The method makes use of specific knowledge regarding white matter lesions, such as that T1 and T2 intensity signatures of white matter lesions act in unison. More specifically, as a region of white matter initially becomes abnormal, it exhibits T2 hyperintensity. T1 hypointensity may or may not accompany this initial T2 hyperintensity. As the T2 hyperintensity accumulates, T1 hypointensity begins to accumulate more rapidly. As mentioned, at the extreme limit of abnormality, white matter comes to resemble CSF in terms of its T1-T2 intensity profile. Furthermore, in the case of partial voluming, that is, the boundary between two regions of pure tissue transects a given voxel, the fractional membership in each of the tissues is equal to the fractional position along the line connecting the centroids of the two tissues: CSF and NAWM, in T1-T2 feature space. In the case of partial character, there is some deviation to the right of the line connecting the two centroids, although the feature space fractional distance approach still provides a useful methodology for computing membership.

Figure 14:
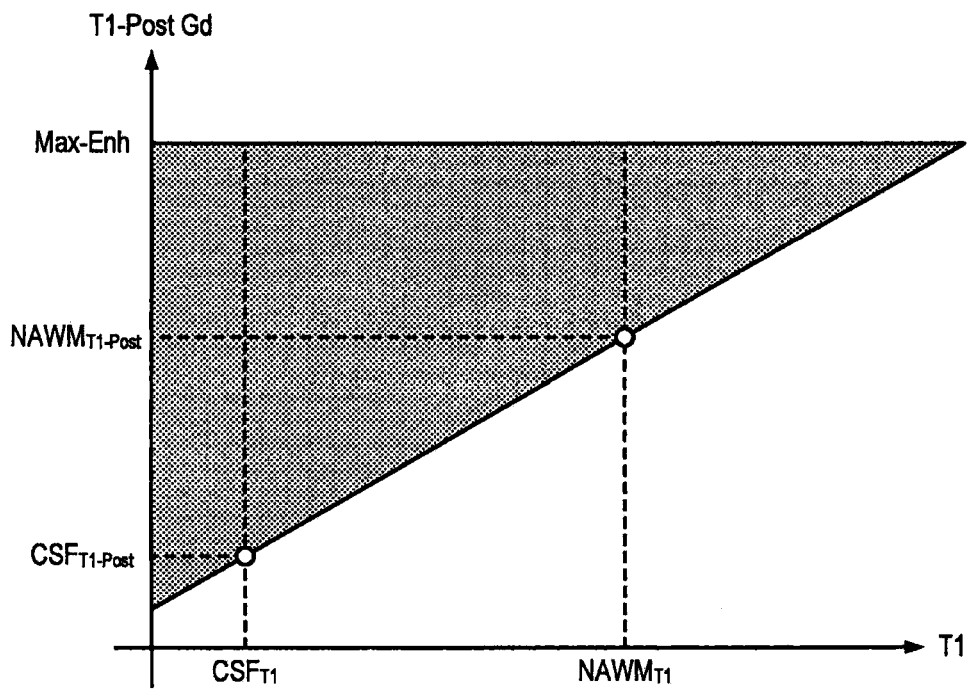
FIGS. 14-17 depict an exemplary method used to quantify membership in the class "enhancing lesion"

Referring now to FIG. 14, the method used to quantify membership in the class, "enhancing lesion," is demonstrated. First, the method uses the knowledge that T1, and T1-Post are the same pulse sequence, although they may possess different acquisition parameters, with the principal difference between the two images being that prior to acquisition of the T1-Post sequence, an intravenous contrast medium is administered, which causes regions of blood brain barrier (BBB) breakdown to exhibit heightened image intensity in the T1-Post image. The intensity of non-enhancing regions, that is, regions where the BBB is not in the process of breaking down, will therefore always lie along the line crossing the CSF and NAWM centroids in T1-T1-Post feature space. On the other hand, the intensity of voxels representing regions where the BBB is in a state of breakdown should lie above this line in T1-T1-Post feature space. In FIG. 14, the CSF and NAWM centroids are shown as small circles, and the line crossing these centroids is additionally shown. Furthermore, there is a maximal intensity which may be observed in the T1-Post sequence due to the presence of contrast medium within the space represented by a voxel. Within the range of contrast concentrations likely to be seen in enhancing tissue, the intensity in the T1-Post sequence of some voxel representing white matter is expected to lie either on the line crossing the CSF and NAWM centroids, for no enhancement. Above the line but below the horizontal "Max-Enh" line shown in the FIG. 14, for some degree of enhancement, or along the "Max-Enh" line, for maximal enhancement.

Figure 15:
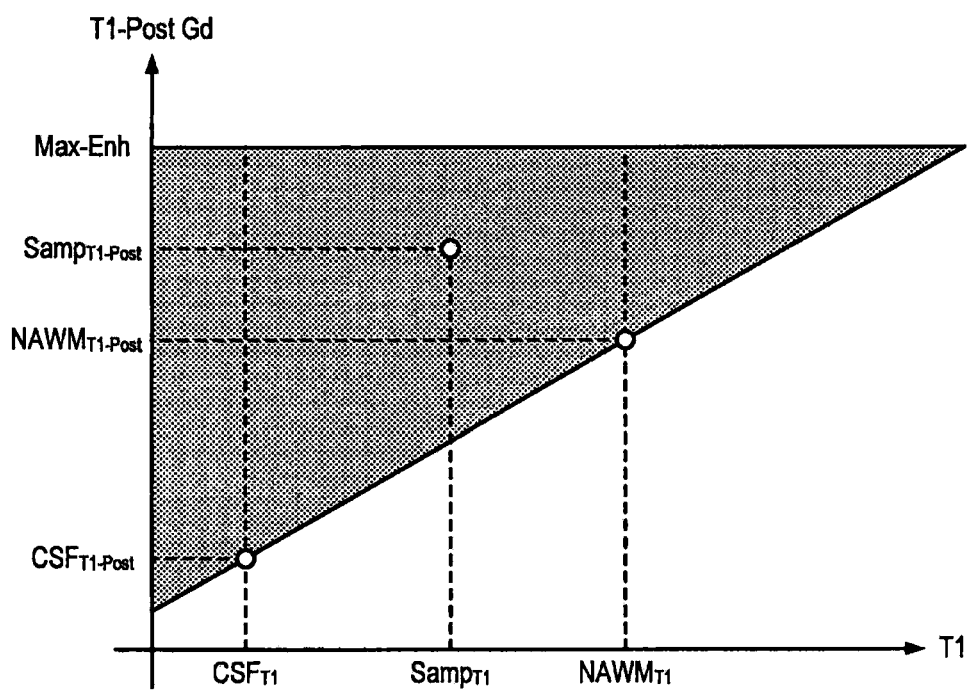
Figure 16:
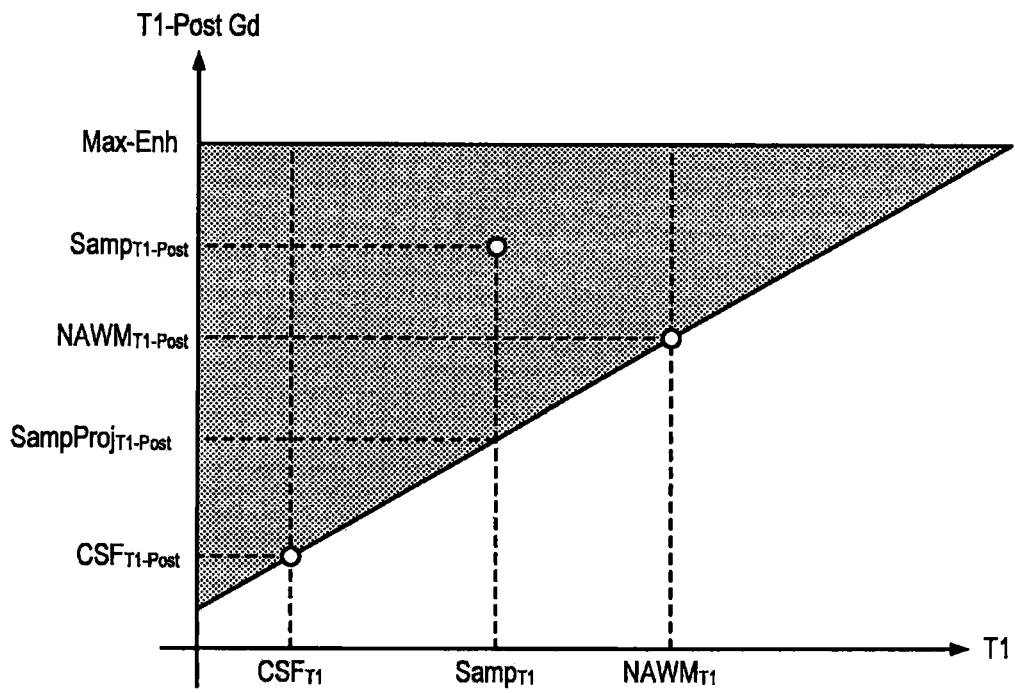
Figure 17:
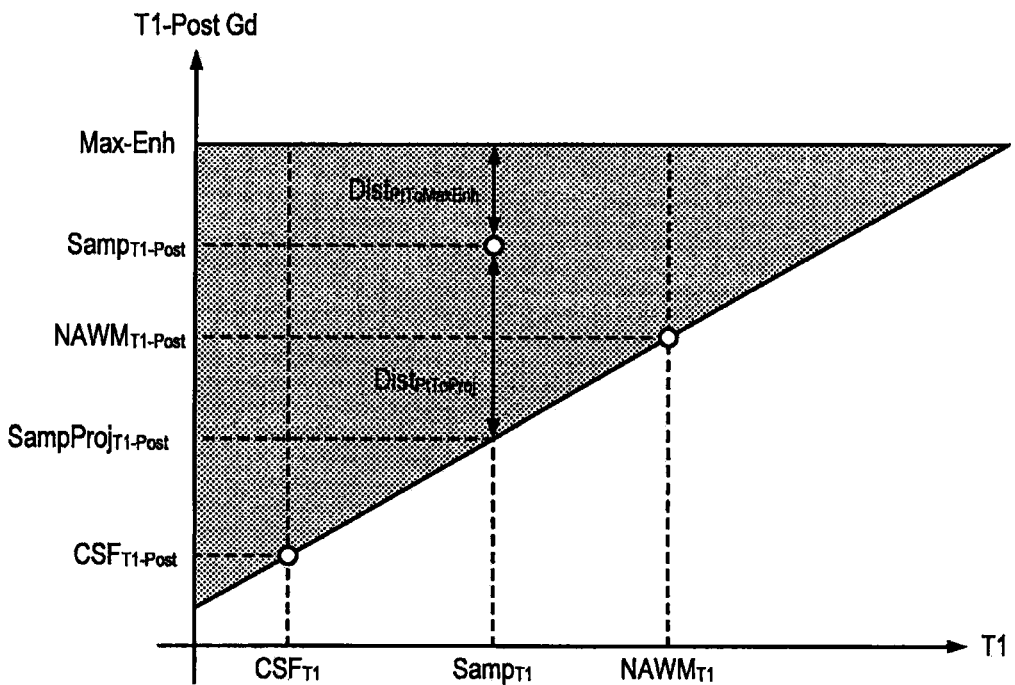

The degree of enhancement is quantified as if it were a linear effect. That is, the fractional distance along the line connecting the point's vertical projection on the CSF-NAWM line, and the point's vertical projection on the "Max-Enh" line, provide that voxel's membership in the class, "enhancing lesion." This process is shown graphically in FIGS. 12-15. In FIG. 15, a trial point is shown by a small circle in the interior of the gray region. In order to quantify the degree of enhancement exhibited by the voxel, the voxel is first projected vertically on the CSF-NAWM line, as shown in FIG. 16. This provides the intensity in the T1-Post sequence that would be observed if the voxel exhibited no enhancement. The fractional distance of the point in question along the vertical line connecting this projection and the "Max-Enh" line is shown graphically in FIG. 17. The vertical distance to the "Max-Enh" line, and the CSF-NAWM line are used to compute the voxel's membership in the enhancing lesion class using the following equation:

$$membership_{EnhancingLesion} = \frac{Dist_{PtToProj}}{Dist_{PtToMaxEnh} + Dist_{PtToProj}}. \quad (3)$$

It should be observed that the trial voxel shown in FIG. 14-17 exhibits some degree of T1 hypointensity. This is clear from the fact that the trial point lies to the left of the NAWM centroid in the figures. However, because the method uses the T1 sequence as a basis against which the T1-Post intensity is judged, this hypointensity has no effect on the computation of enhancing lesion membership of that voxel. It should be noted, furthermore, that this normalization method works for elevated T1 intensities, as well. Blood in the region represented by a voxel does not have any effect upon the computed membership of the voxel in the class "enhancing lesion," for the same reason. It should further be noted that if the T1-Post Gd image were acquired with magnetization transfer suppression enabled, then the T1 sequence on the X-axis of FIGS. 14-17 would be substituted with a T1 sequence also acquired with magnetization transfer suppression enabled. In this way, mildly bright regions, due to T2 lesions and not due to enhancement, would still lie along the line connecting the CSF NAWM line, but above and to the right of the NAWM centroid, and would be correctly quantified as not possessing any enhancement.

In certain embodiments, individual steps recited in FIGS. 12-17 may be combined, eliminated, or reordered. In other embodiments, instructions, such as instructions provided in FIGS. 12-17, may reside in computer readable medium wherein those instructions are executed by a processor to perform one or more of processes recited in FIGS. 12-17. In still other embodiments, the instructions may reside in any other computer program product, where those instructions are executed by a computer external to, or internal to, data storage system, to perform one or more of steps recited in FIGS. 12-17. In either case, the instructions may be encoded in computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

Lesion Change Detection

The lesion change detection algorithm provides, when viewed visually as part of an application, a mechanism for the user to inspect the output of any registration algorithm used, and, if the results are unsatisfactory, allows the user to rerun the registration algorithm. Further, the lesion change detection algorithm allows the user to inspect the output of the automatic parenchyma mask generator, and to edit the mask as appropriate.

Figure 18:
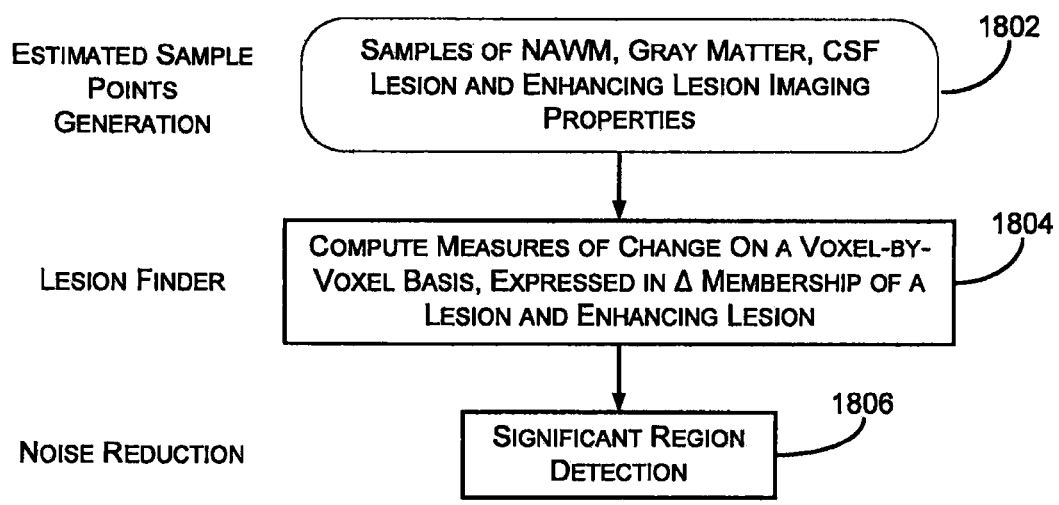
FIG. 18 is an exemplary flowchart illustrating the lesion change detection method.

Referring now to FIG. 18, the lesion change detection method includes three primary steps. First, as indicated by resource block 1802, the sample points generated by the automated algorithm described in FIGS. 7-11 are used. These same points define NAWM, CSF, and grey matter. The process of obtaining sample points, as described above, includes first acquiring images in a manner consistent with the ultimate objective, in this context the detection of a change in a lesion. This means, for example, that intravenous (IV) contrast should be administered in each acquisitions at the same time relative to image acquisition, or at a time during the image acquisition such that any difference between the acquisitions do no impact the appearance of the contrast in the images. Other acquisition-related issues which may be considered and addressed include: reducing the slice thickness, in particular, to limit the number of tissues which might be included in individual voxels; eliminating inter-slice gaps as the gaps correspond to regions of the brain where there is no information from which to compute changes and the presence of inter-slice gaps make it impossible to correct for registration errors in the through-slice direction, performing 3D acquisition; acquiring the images using an equivalent scanner, scanner software, pulse sequences, and acquisition parameters, correcting for decay of gradient coils; correcting for inhomogeneities at the time of acquisition to the greatest degree possible; and acquiring the images as close to spatially registered as possible as frequently registration algorithms introduce artifacts in proportion with the degree of difference between the images being registered.

As further indicated in resource block 1802, the mathematical description of the lesion and enhanced lesion imaging properties of the particular images generated by the process described in FIGS. 12-17 are also used.

At block 1804, the system measures of change are computed on a voxel-by-voxel basis. These are expressed in normalized Δ membership form. Finally, at process block 1806, a noise reduction step is performed as will be described in detail below. Due to noise and other factors, virtually all voxels will demonstrate changes of some sort. Only changes due to the underlying disease process are of interest, however, and therefore the purpose of this step is to separate disease related changes from non disease related changes. In order to do this, the method automatically identifies strongly spatially connected regions that are changing in the same way, and then applies a kind of test of "significance," such that changes small in magnitude but of large spatial extent may be identified as significant, and likewise changes small in spatial extent but large in magnitude may also be correctly identified as real. The process by which significant regions are identified is described in detailed below in conjunction with FIGS. 19-23.

In certain embodiments, individual steps recited in FIG. 18 may be combined, eliminated, or reordered. In other embodiments, instructions, such as instructions provided in FIG. 18, may reside in computer readable medium wherein those instructions are executed by a processor to perform one or more of processes recited in FIG. 18. In still other embodiments, the instructions may reside in any other computer program product, where those instructions are executed by a computer external to, or internal to, data storage system, to perform one or more of steps recited in FIG. 18. In either case, the instructions may be encoded in computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

Significant Region Detection/Identification

The subsequently disclosed algorithm computationally defines significance in two and three dimensional image volumes as objects in noisy images which differ significantly from the background noise. By using this definition of significance in the course of reviewing image volumes containing zero mean noise and optional object regions, object regions can be automatically and reproducibly identified with a very high sensitivity and specificity. As will be clear to one of ordinary skill in the art, the present algorithm is a substantial improvement over prior algorithms, as it includes the disclosure of a training step allowing the algorithm to generate a quantitative definition of significance without explicitly modeling the noise. Prior methods were limited to using empirically derived definitions.

As will also become clear, the subsequently disclosed algorithm uses three pieces of knowledge: that real objects tend to be clumpy, rather than long and winding, that the larger an object is, the more likely it is to be real and not the result of noise alone, and that objects with bright regions are more likely to be real. By defining significance within the context of these known facts, mathematical precision is added. Furthermore, the training algorithm used to generate this definition is highly flexible in that it is useable for data which possesses noise which is spatially correlated and/or non-Gaussian. As mentioned, the training algorithm is automatic and does not require explicit modeling of the noise. Further, compared with the previously used methods of thresholding and Gaussian blur/thresholding, the subsequently disclosed algorithm is able to identify far subtler objects, exhibits more controlled smearing of bright objects into the surrounding space, and does not require the tuning of parameters.

Figure 19:
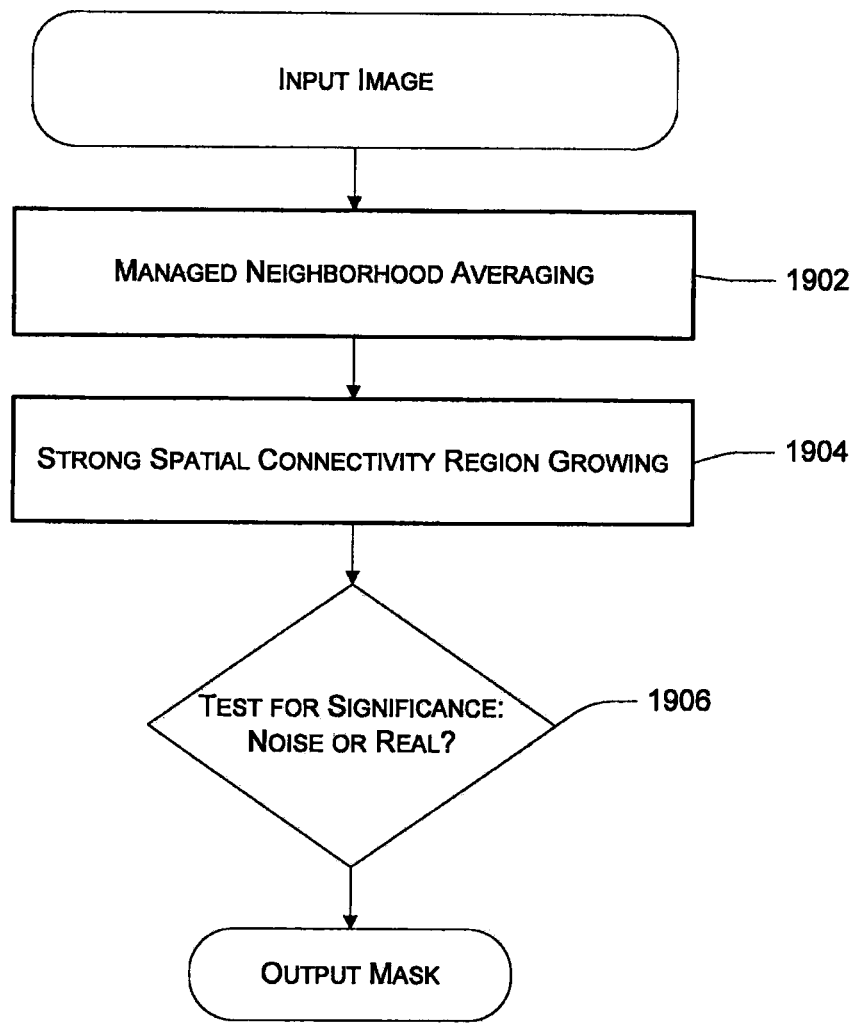
FIG. 19 is an exemplary high-level flowchart depicting the process of identifying significant regions.

Turning now to FIG. 19, an exemplary high level flowchart is presented which breaks the identification of significant regions into three components: a managed neighborhood averaging stage at process block 1902, a strong special connectivity region growing component at process block 1904, and a test for significance at process block 1906, which is executed during each iteration of the strong spatial connectivity region growing algorithm.

The managed neighborhood averaging sub-algorithm at process block 1902 is part blurring algorithm, although it uses multiple kernels, multiple heuristics, and takes additional actions beyond blurring. This sub-algorithm identifies and suppresses some regions whose non-zero intensities are highly likely to be entirely due to noise—which is to be contrasted with traditional uses of blurring kernels in object identification, where the blurring kernels are used to differentiate between object and non-object voxels directly (through the use of a threshold). In the present context, the managed neighborhood averaging step is only a 'front-end', to be followed by the strong spatial connectivity region growing and test for significance steps. The managed neighborhood average breaks up and suppresses at least some of the empty regions, but with nearly no inadvertent suppression of real objects, the real decision-making is left to the subsequent step. The managed-neighborhood averaging algorithm additionally avoids smearing of very bright objects into their surroundings (a problem which is endemic to traditional blurring methods), via the exclusion of voxels with magnitude intensities greater than or equal to $4\sigma$ from the neighborhood average calculations. In addition to identification of noise regions, this sub-algorithm identifies voxels which might belong to objects possessing opposite numerical signs, based on their neighborhoods (e.g., negative valued voxels belonging to positive valued objects, and vice versa).

Figure 20:
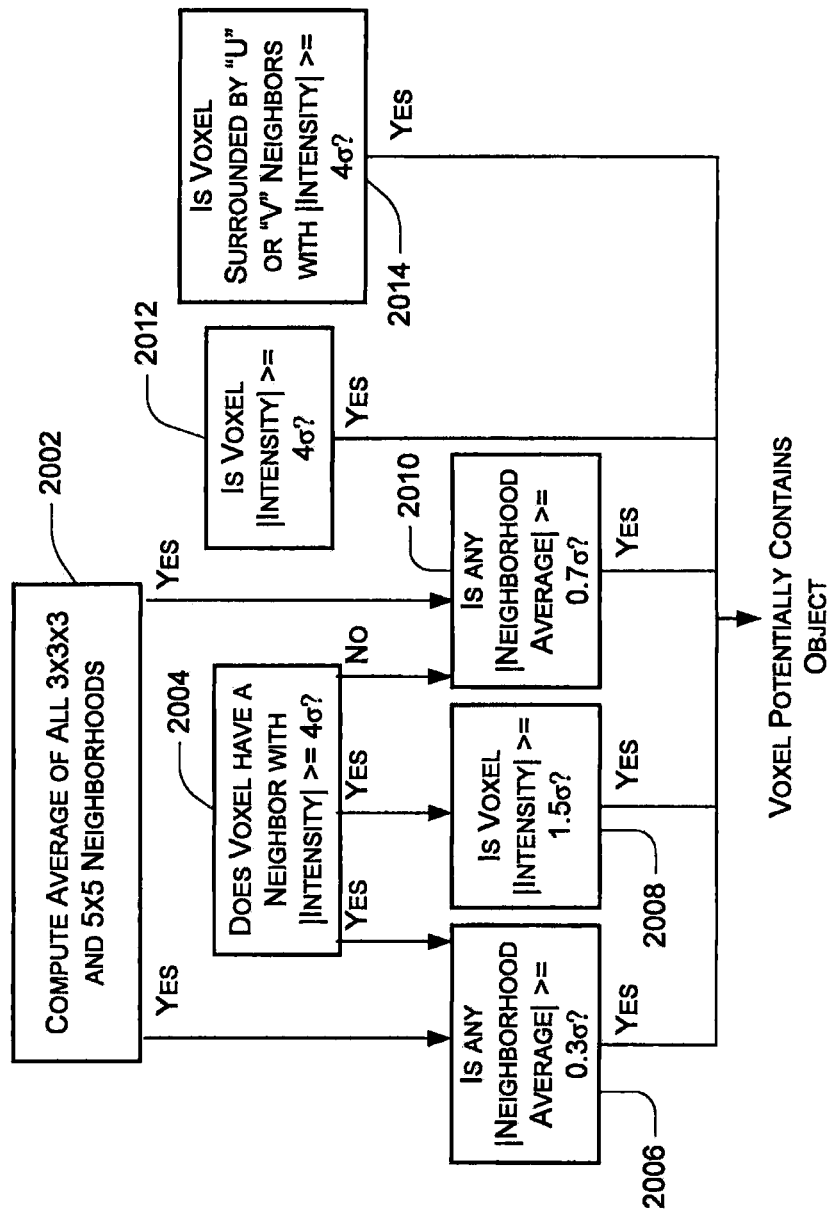
FIG. 20 is an exemplary flowchart depicting the managed-neighborhood algorithm shown in FIG. 19.

FIG. 20 provides an exemplary embodiment of the managed-neighborhood averaging algorithm. The left hand-side contains the component of the managed neighborhood averaging function which executes blurring operations. Neighborhood averages are computed for each voxel in the image, for 3×3×3 regions (3D), and for 5×5 regions (2D) in each of the three fundamental imaging planes, as indicated by block 2002. These averages exclude from their calculations any voxels which possess magnitude intensities greater than or equal to $4\sigma$. The purpose of this stipulation is to focus the attention of this part of the algorithm on voxels which are probably not object (i.e., because voxels with magnitude intensities greater than or equal to $4\sigma$ are likely to contain object, based on the cumulative distribution function of a Gaussian) and to avoid introducing any 'blooming' which is characteristic of traditional blurring algorithms (and which would otherwise be a major problem in light of the use of large unweighted 5×5 kernels). The algorithm additionally determines which voxels have at least one neighbor with magnitude intensity $>=4\sigma$ (i.e., such neighbors probably contain real object), as indicated in block 2004. For each voxel which has a neighbor with greater than or equal to $4\sigma$, the algorithm retains the voxel for further consideration if the magnitude of any of its four neighborhood averages are greater than or equal to $0.3\sigma$ (a very lenient criteria), as indicated in block 2006, or if the voxel itself possesses an intensity $>=1.5\ \sigma$ (still a fairly lenient criteria), as indicated in block 2008. If the voxel does not have a neighbor with a magnitude intensity greater than or equal to $4\sigma$, then a slightly (though barely) more stringent criteria, that at least one of the neighborhood averages is greater than or equal to $0.7\sigma$ is required for the voxel to be retained for further consideration, as indicated by block 2010. Examining the right half of FIG. 20, if the voxel itself possesses a magnitude intensity greater than or equal to $4\sigma$, it is automatically retained for further consideration, as indicated by block 2012. If the voxel is surrounded by a U or V shaped region of neighbors with magnitude intensity greater than or equal to 4σ, it is also retained for further consideration, as indicated by block 2014. The parameters were determined empirically in consideration of the statistical properties of the Gaussian distribution.

Figure 21:
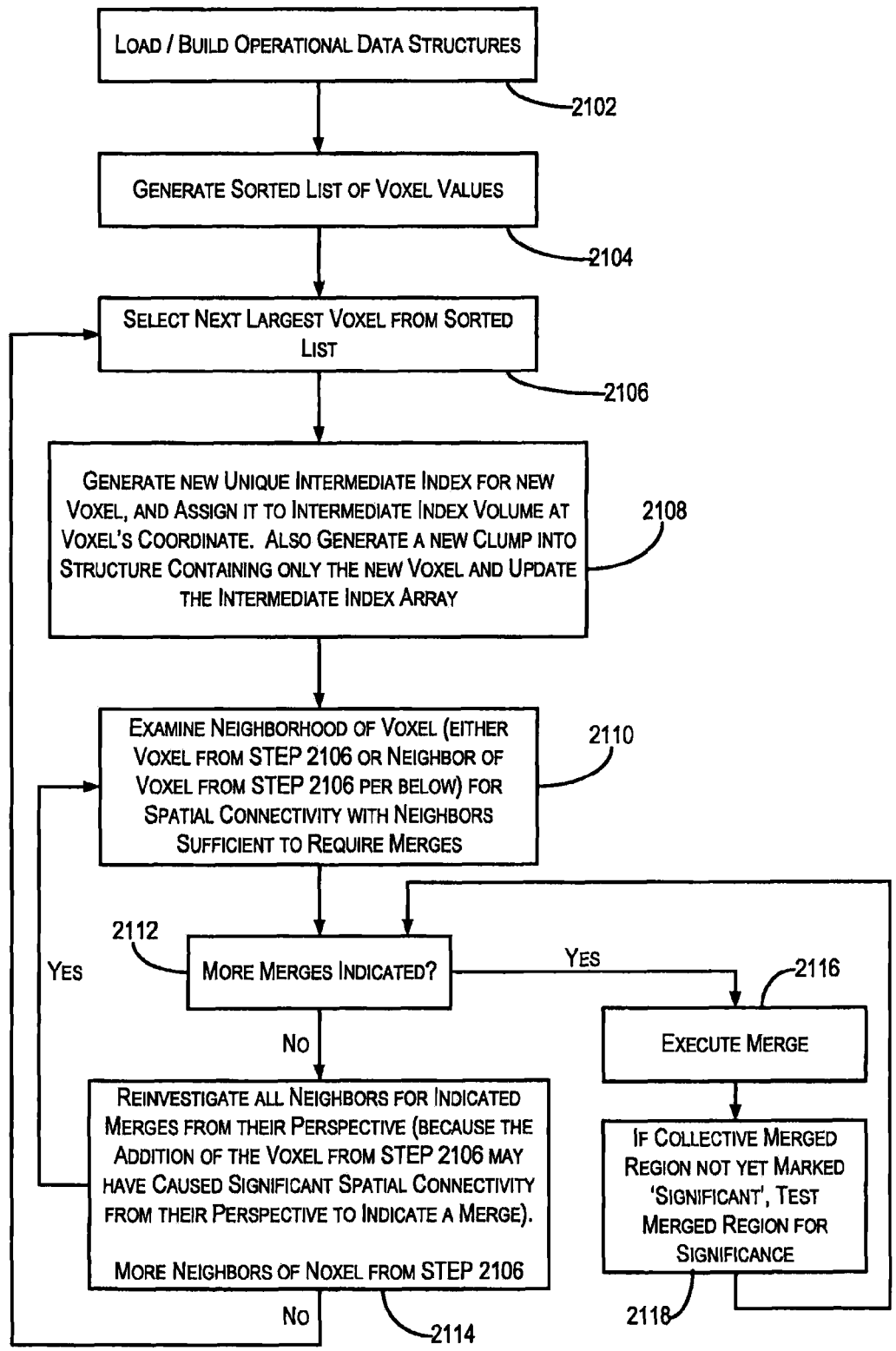
FIG. 21 is an exemplary flowchart depicting the strong spatial connectivity region growing and test of significance algorithms shown in FIG. 19.

FIG. 21 shows the implementation of the strong spatial connectivity region growing and test of significance algorithms, which are executed in an alternating iterative fashion. First, at block 2102, the operational data structures are either built, in the case of the simple structures, or loaded, in cases where the complexity of the structure is too great to be constructed at each instantiation, such as the case of the look-up table. Next, the image volume that is to be explored for regions of signal is examined at block 2104. If regions with positive intensities are to be identified, then all voxels with positive intensities are loaded into a doubly linked list, which is subsequently sorted according to intensity.

A control loop is then commenced beginning at block 2106. At each instance of this loop, the next largest voxel is selected from the doubly linked list. At block 2108, the selected voxel coordinate is assigned a unique number, which will be referred to as an "intermediate index." The details and purpose of this intermediate index are discussed below. The intermediate index is recorded at the coordinates of the original voxel, but in a separate volume. A new clump information descriptor is created for the voxel, and appropriate data structures are updated. The term 'clump' is being used, here, to describe a strongly spatially connected region of signal. Now, at block 2110, the neighborhood of the new voxel is then examined, in order to determine whether the new voxel is sufficiently strongly connected, for example, sufficiently surrounded, by its neighbors to warrant merging into a larger clump with them. This is the strong spatial connectivity requirement alluded to, above. The specific details of this constraint are relatively complicated and are extremely central to the functioning of this method. They are described in detail below.

At blocks 2112 and 2114, the voxel and its clump, as it comes to belong to a clump, are merged with neighboring voxels and their clumps, if the neighboring voxels belong to clumps, as allowed by the strong spatial connectivity constraint. Furthermore, with the addition of each new voxel, the neighbors of the new voxel are re-tested for indicated merges from their perspective, since the addition of the new voxel may have been all that was needed to satisfy their spatial connectivity constraint. Note that each time a merge is performed, if the contributing clumps have already been judged to be significant, then the collective clump is also judged to be significant. At block 2114, if the new clump has not inherited significance from one of the clumps that contributed to its creation, the new collective clump is tested for significance. It should be underscored that once a clump has met the criteria of significance, it confers significance on any clump to which it is subsequently merged (2116). This means that a small but significant region surrounded by a penumbra of very low intensity will be collectively significant, even if the region as a whole does not meet the significance criteria. After this, block 2118 is reached and the main loop returns to its beginning, and selects the next largest voxel from the list, and the process is repeated.

Figure 22:
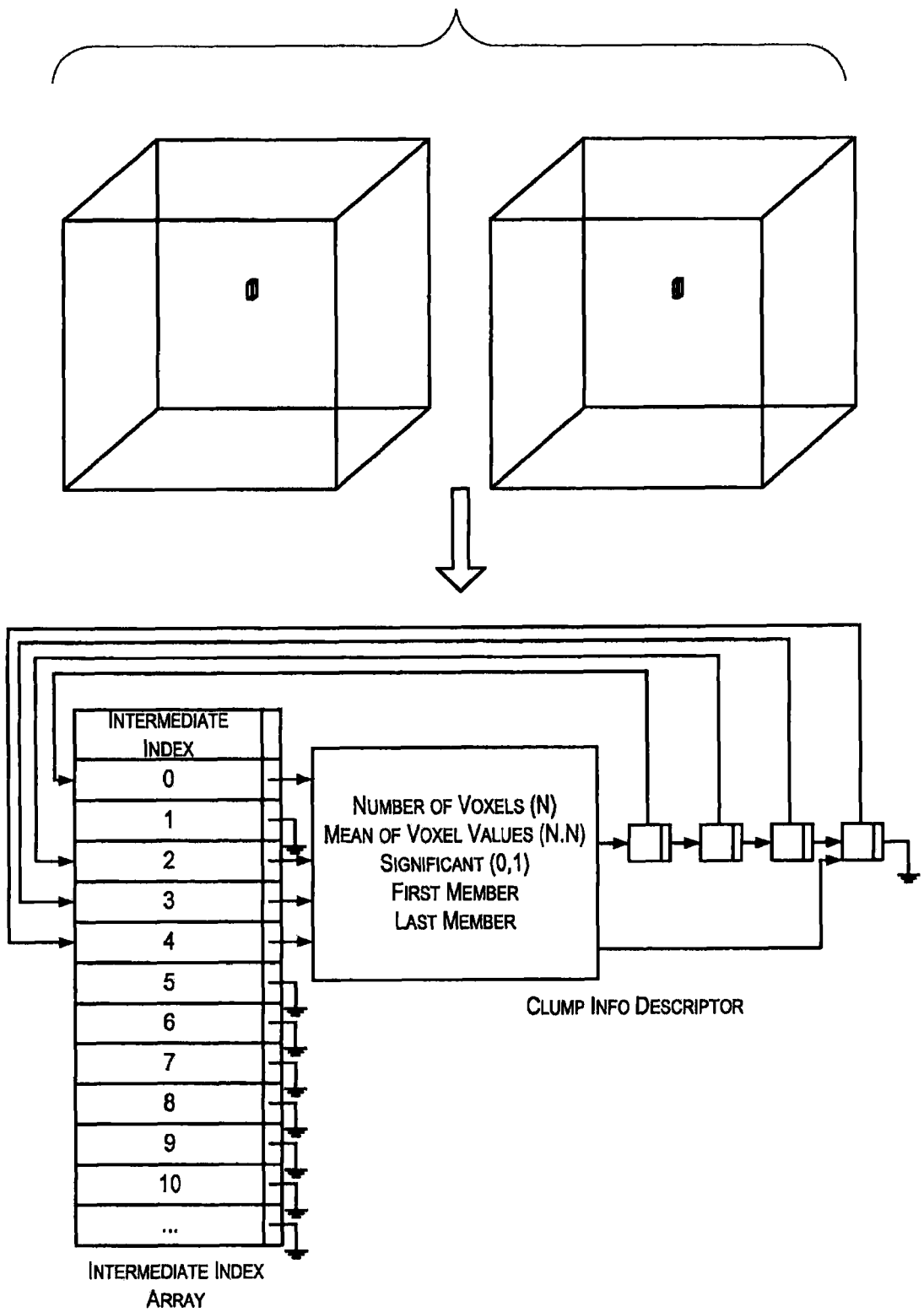
FIG. 22 is an exemplary depiction of a data structure to facilitate efficient marching of clumps in the process depicted in FIG. 21.

The purpose of the data structure shown in FIG. 22 is to facilitate very efficient merging of clumps, which is a task performed a very large number of times during the execution of the main loop in FIG. 21. In addition to keeping track of statistics for each clump, for example, number of voxels, mean of the voxel values, and whether or not the clump has been judged to be significant, the structure is fundamentally circular. That is, using this structure, it can be determined very rapidly which clump a given voxel belongs to, and it can be likewise determined very rapidly which voxels belong to a clump. Furthermore, using this structure, the process of reassigning a list, potentially a very large list, of voxels from one clump to another is extremely rapid. The purpose of the volume of intermediate indices and intermediate index array, as opposed to simply using a volume of pointers, is reduced memory utilization. A 512×512×48 volume has over 12.5 million voxels. A 512×512×144 volume has almost 38 million voxels. In any given volume to be inspected, it is likely that only a fraction of these will have "on" values. Based on this fact, and the likely difference in memory space required to store an index versus a pointer, the given approach was adopted. If memory utilization were not an issue, however, the concept of intermediate index could be abandoned, and the volume of intermediate indices and intermediate index array could be replaced with a volume of pointers to clump info descriptors.

Figure 23:
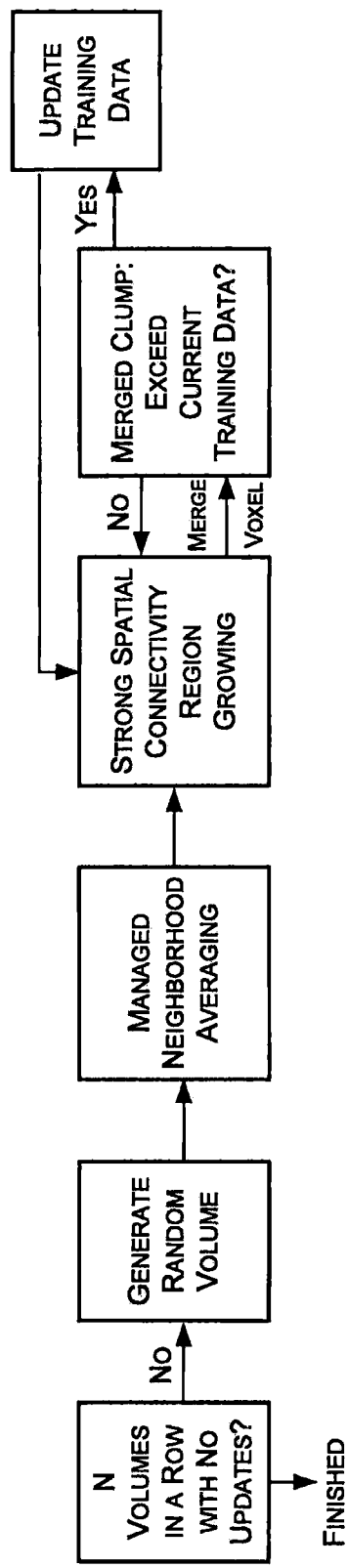
FIG. 23 is an exemplary flowchart illustrating the process by which the algorithm of FIG. 19 is trained.

Turning to FIG. 23, an exemplary flowchart is presented for training the algorithm. The algorithm is trained by showing it a series of 100×100×100 voxel volumes containing only random Gaussian noise. This process is similar to the process of actually executing the significant region detector, except that during training, the algorithm knows that any clumps observed are definitely due to noise alone (since there are no objects contained in the random volumes) and thus after every merge, the number of voxels in the newly merged clump, and its mean intensity, are compared with the definition of significance. If the newly discovered clump possesses a higher mean intensity than that in the definition of significance, then the definition of significance is raised to the newly discovered level, such that when the algorithm is run (i.e. not in training mode) any future clumps of that size, possessing the same mean intensity, will not be judged significant. This process of showing random volumes to the training algorithm to allow it to see what voxel intensities and configurations may occur due to noise continues until one million volumes in a row have been shown to the algorithm, with no updates to the definition of significance. This training process has to be performed only once for a given noise type (e.g. spatially uncorrelated Gaussian noise)—once performed, the training data may be applied to an unlimited number of volumes which share the same noise profile.

The process illustrated in conjunction with FIGS. 19-23 are described in the context of reduction of noise/identification of "significant" regions within change detection brain MRI images. The method's ability to identify such regions within noise fields, particularly regions whose amplitude lies below the level of the noise floor, presents possible applications far beyond this domain. The method should, in fact, find application in a large number of image processing fields. Specifically it should find application in any case where subtle regions of signal, which may be below the noise floor but which exhibit spatial connectedness, exist. These include a potential unlimited number of applications, of course, including a range of areas of change detection, such as medical analysis, remote sensing, astronomy, geology, surveillance, classification, and the like. There are many potential applications for the method within medical imaging, but beyond change detection, for example, the algorithm has been used extensively to aid in automated sample point definition, and in lesion finding as described above.

In certain embodiments, individual steps recited in FIGS. 19-23 may be combined, eliminated, or reordered. In other embodiments, instructions, such as instructions provided in FIGS. 19-23, may reside in computer readable medium wherein those instructions are executed by a processor to perform one or more of processes recited in FIGS. 19-23. In still other embodiments, the instructions may reside in any other computer program product, where those instructions are executed by a computer external to, or internal to, data storage system, to perform one or more of steps recited in FIGS. 19-23. In either case, the instructions may be encoded in computer readable medium comprising, for example, a magnetic information storage medium, an optical information storage medium, an electronic information storage medium, and the like. "Electronic storage media," may mean, for example and without limitation, one or more devices, such as and without limitation, a PROM, EPROM, EEPROM, Flash PROM, compactflash, smartmedia, and the like.

There are a number of important differences between this method and prior methods. First, prior automated sample point algorithms are only "maximally" automated, requiring the manual provision of samples of normal appearing white matter, while the current algorithm is automated, not requiring that any samples be supplied by the user. This is a very important point, considering the time involved in defining samples, the variability that manual definition of these samples introduces, and the training issues involved. Second, prior algorithms often require the use of a specific imaging protocol. Generally, requiring that images be acquired with a very specific protocol is both unnecessarily restrictive, and unrealistic. The present method is extremely flexible with regard to acquisition parameters. Third, prior algorithms are only applicable to brain tumors, while the present method is applicable to multiple sclerosis, metastatic brain tumors from non-brain primaries, and other forms of white matter pathology. Fourth, prior algorithms use a fluid attenuation by inversion recovery (FLAIR) sequence whereas the current method uses T2, instead. Use of T2 instead of FLAIR makes the algorithm more sensitive, because T2 is monotonic with regard to lesion development. Generally speaking, the more pathological a region is, the higher its intensity in T2, which contrasts with FLAIR, where as a region of white matter becomes more abnormal, it first increases in intensity, but then subsequently decreases, as it acquires a more fluidic character. FLAIR additionally suffers frequently from fluid suppression artifact, a problem that T2 is not susceptible to since it does not suppress fluid. Generally speaking, the use of T2 in lieu of FLAIR makes the definition of lesion imaging characteristics much more consistent, and thus makes the algorithm much more robust, that is, sensitive, reliable, consistent, and flexible with regard to the particulars of specific image acquisitions. Fifth, the present method uses a very different model of lesion and enhancing lesion imaging characteristics, which is more "correct." The approach taken by the present method is thus more sensitive and accurate.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for automatically generating sample points from series of medical images and identifying a significant region comprising:
   an image acquisition system configured to acquire the series of medical images of a region of interest (ROI) in a subject;
   an automated mask generator configured to review the series of medical images and automatically generate a parenchyma mask, wherein the parenchyma mask is used to designate sample points;
   an automated sample point generator configured to review the series of medical images and automatically detect portions of the series of medical images indicative of a material expected to be in the ROI and designate sample points therefrom using the parenchyma mask;
   a target-tissue identification system configured to utilize the sample points to create a mathematical description of a target tissue and an enhanced target tissue thin the series of medical images;
   a target-tissue change detection system configured to detect a change in the mathematical description of the target tissue within the series of medical images from a prior mathematical description of the target tissue within a prior series of medical images;
   a significant region detector to automatically identify a significant object in the series of medical images, wherein the significant region detector includes a training algorithm that generates a quantitative definition of significance; and
   wherein the automated mask generator is configured to construct a single-intensity histogram, apply a fish-bowl algorithm to find an air threshold, and, once the air threshold has been determined, generate an initial parenchyma mask by eliminating air using the thresholds provided by the fish-bowl algorithm.

2. The system of claim 1 wherein the automated mask generator is further configured to review the series of medical images and automatically generate a cerebrospinal fluid (CSF) mask.

3. The system of claim 1 further including a registration system configured to spatially register the series of medical images to one another at a sub-voxel level to establish a common spatial framework.

4. The system of claim 1 wherein the parenchyma mask is a brain parenchyma mask.

5. The system of claim 1 wherein the automated sample point generator is configured to find CSF samples, and use the CSF samples to identify white matter, white/grey matter, and/or grey matter sample points.

6. The system of claim 1 wherein the target tissue is a lesion and wherein the target-tissue change detection system is configured to compute measures of change on a voxel-by-voxel basis, and express the change in a normalized Δ membership form.

7. The system of claim 1 wherein the series of medical images include at least one of MRI images and CT images.

8. The system of claim 1 wherein the material indicative of a material expected to be in the ROI includes cerebral spinal fluid (CSF), white matter, gray matter, bone, and lesions.

9. A system for automatically generating sample points from series of medical images and identifying a significant region cormprising:
   an automated sample point generator configured to review a series of medical images and automatically detect portions of the series of medical images indicative of a material expected to be in a ROI included in each of the series of medical images and designate sample points within the series of medical images therefrom;
   a lesion identification system configured to utilize the sample points to create a mathematical description of a lesion and an enhanced lesion within the series of medical images;
   a lesion change detection system configured to detect a change in the mathematical description of the lesion within the series of medical images from a prior mathematical description of the lesion within a prior series of medical images;

a significant region detector to automatically identify a significant object in the series of medical images wherein the significant region detector includes a training process that generates a quantitative definition of significance; and wherein the training process is configured to show random volumes to a training algorithm to allow the training algorithm to see what voxel intensities and configurations may occur due to noise, and continue to show random volumes to the training algorithm until a predetermined amount of random volumes in a row is shown to the training algorithm without an update to the definition of significance.

10. A method for automatically generating sample points from series of medical images and identifying significant region comprising the steps of:
   a) acquiring a series of medical images of a region of interest (ROI) in a subject;
   b) automatically reviewing the series of medical images and automatically generating a brain parenchyma mask therefrom, wherein automatically generating the brain parenchyma mask includes constructing a single-intensity histogram, applying a fish-bowl algorithm for finding the appropriate air threshold, and once the air threshold has been determined, generating an initial parenchyma mask by eliminating air using the thresholds provided by the fish-bowl alsorithm, and using the brain parenchyma mask for designating sample points;
   c) automatically reviewing the series of medical images and automatically detecting portions of the series of medical images indicative of a material expected to be in the ROI and designating sample points therefrom using the brain parenchyma mask;
   d) utilizing the sample points for creating a mathematical description of a lesion and an enhanced lesion within the series of medical images;
   e) detecting a change in the mathematical description of the lesion within the series of medical images from a prior mathematical description of the lesion within a prior series of medical images; and
   f) automatically identifying a significant region in the series of medical images.

11. The method of claim 10 wherein step b) further includes spatially registering the series of medical images to one another at a sub-voxel level to establish a common spatial framework.

12. The method of claim 10 wherein automatically identifying a significant region in step f) further includes utilizing a managed neighborhood averaging algorithm, growing a strong spatial connectivity region, and testing for significance.

13. A method for automatically generating sample points from series of medical images and identifying a significant region comprising the steps of:
   a) acquiring a series of medical images of a region of interest (ROI) in a subject;
   b automatically reviewing the series of medical images and automatically generating a brain parenchyma mask therefrom, and using the brain parenchyma mask for designating sample points;
   c) automatically reviewing the series of medical images and automatically detecting portions of the series of medical images indicative of a material expected to be in the ROI and designating sample points therefrom using the brain parenchyma mask;
   d) utilizing the sample points for creating a mathematical description of a lesion and an enhanced lesion within the series of medical images;
   e) detecting a change in the mathematical description of the lesion within the series of medical images from a prior mathematical description of the lesion within a prior series of medical images;
   f) automatically identifying a significant region in the series of medical images; and
   g) utilizing training process for generating a quantitative definition of significance without modeling noise.

14. A method for automatically generating sample points from a series of medical images and identifying a significant region comprising the steps of:
   a) acquiring a series of medical images of a region of interest (ROI) in a subject;
   b) automatically reviewing the series of medical images and automatically generating brain parenchyma mask therefrom and using the brain parenchyma mask or designating sample points;
   c) automatically reviewing the series of medical images and automatically detecting portions of the series of medical images indicative of a material expected to be in the ROI and designating sample points therefrom using the brain parenchyma mask;
   d) utilizing the sample points for creating a mathematical description of a lesion and an enhanced lesion within the series of medical images;
   e) detecting a change in the mathematical description of the lesion within the series of medical images from a prior mathematical description of the lesion within a prior series of medical images;
   f) automatically identifying a significant region in the series of medical images; and
   g) utilizing a training process for generating a quantitative definition of significance without tuning parameters.

15. A method for automatically generating sample points from a series of medical images and identifying a significant region comprising the steps of:
   a) acquiring a series of medical images of a region of interest (ROI) in a subject;
   b) automatically reviewing the series of medical images and automatically generating a brain parenchyma mask therefrom, and using the brain parenchyma mask for designating sample points;
   c) automatically reviewing the series of medical images and automatically detecting portions of the series of medical images indicative of a material expected to be in the ROI and designating sample points therefrom using the brain parenchyma mask;
   d) utilizing the sample points for creating a mathematical description of a lesion and an enhanced lesion within the series of medical images;
   e) detecting a change in the mathematical description of the lesion within the series of medical images from a prior mathematical description of the lesion within a prior series of medical images;
   f) automatically identifying a significant region in the series of medical images; and
   g) utilizing a training process for generatng a quantitative definition of significance and
   showing random volumes to a training algorithm for allowing the training algorithm to see what voxel intensities and configurations may occur due to noise, and continuing showing random volumes to the training algorithm until a predetermined amount of random volumes in a row have been shown to the training algorithm without updating the definition of significance.

\* \* \* \* \*

UNITED STATES PATENT AND TRADEMARK OFFICE
CERTIFICATE OF CORRECTION

PATENT NO.         : 8,600,135 B2
APPLICATION NO.    : 12/648132
DATED              : December 3, 2013
INVENTOR(S)        : Patriarche et al.

It is certified that error appears in the above-identified patent and that said Letters Patent is hereby corrected as shown below:

In the Claims

Column 30, Claim 9, line 52, "cormprising" should be --comprising--.

Column 31, Claim 10, line 16, "from series" should be --from a series--.

Column 31, Claim 10, line 16, "identifying significant" should be --identifying a significant--.

Column 31, Claim 10, line 28, "alsorithm" should be --algorithm--.

Column 32, Claim 13, line 11, "utilizing training" should be --utilizing a training--.

Column 32, Claim 14, line 19, "generating brain" should be --generating a brain--.

Column 32, Claim 14, line 20, "mask or" should be --mask for--.

Column 32, Claim 15, line 61, "generatng" should be --generating--.

Signed and Sealed this
Eleventh Day of March, 2014

Michelle K. Lee
*Deputy Director of the United States Patent and Trademark Office*